United States Patent
Vidlund et al.

(10) Patent No.: US 6,616,684 B1
(45) Date of Patent: Sep. 9, 2003

(54) ENDOVASCULAR SPLINTING DEVICES AND METHODS

(75) Inventors: Robert M. Vidlund, Maplewood, MN (US); Marc A. Simmon, Becker, MN (US); Todd J. Mortier, Minneapolis, MN (US); Cyril J. Schweich, Jr., St. Paul, MN (US); Peter T. Keith, St. Paul, MN (US); Richard F. Schroeder, Fridley, MN (US); Jason Kalgreen, Plymouth, MN (US)

(73) Assignee: Myocor, Inc., Maple Grove, MN (US)

( * ) Notice: Subject to any disclaimer, the term of this patent is extended or adjusted under 35 U.S.C. 154(b) by 0 days.

(21) Appl. No.: 09/679,550

(22) Filed: Oct. 6, 2000

(51) Int. Cl.⁷ .............................................. A61B 17/08
(52) U.S. Cl. ...................................................... 606/213
(58) Field of Search ........................... 606/213; 600/16; 128/898

(56) References Cited

U.S. PATENT DOCUMENTS

| | | |
|---|---|---|
| 4,690,134 A | 9/1987 | Snyders |
| 4,705,040 A | 11/1987 | Mueller et al. |
| 5,104,407 A | 4/1992 | Lam et al. |
| 5,665,092 A | 9/1997 | Mangiardi et al. |
| 5,755,783 A | 5/1998 | Stobie et al. |
| 5,758,663 A | 6/1998 | Wilk et al. |
| 5,800,531 A | 9/1998 | Cosgrove et al. |
| 5,855,601 A | 1/1999 | Bessler et al. |
| 5,902,229 A | 5/1999 | Tsitlik et al. |
| 5,928,281 A | 7/1999 | Huynh et al. |
| 5,961,549 A | 10/1999 | Nguyen et al. |
| 5,971,910 A | 10/1999 | Tsitlik et al. |
| 5,971,911 A | 10/1999 | Wilk |
| 5,972,022 A | 10/1999 | Huxel |
| 5,972,030 A | 10/1999 | Garrison et al. |
| 6,001,126 A | 12/1999 | Nguyen-Thien-Nhon |

(List continued on next page.)

FOREIGN PATENT DOCUMENTS

| | | |
|---|---|---|
| DE | 199 47 885 | 4/2000 |
| EP | 1 129 736 | 9/2001 |
| WO | 97/24082 | 7/1997 |
| WO | 97/24083 | 7/1997 |

(List continued on next page.)

OTHER PUBLICATIONS

US 6,197,052, 3/2001, Cosgrove et al. (withdrawn)
McCarthy, Transcription of Mar. 13, 2000 Presentation by Patrick McCarthy at the American College of Cardiology.
Batista, MD et al., "Partial Left Ventriculectomy to Treat End–Stage Heart Disease", *Ann. Thorac. Surg.*, 64:634–8, 1997.

(List continued on next page.)

Primary Examiner—John J. Calvert
Assistant Examiner—James Smith
(74) Attorney, Agent, or Firm—Finnegan, Henderson, Farabow, Garrett & Dunner, LLP

(57) ABSTRACT

A method for placing a splint assembly transverse a heart chamber includes providing an elongate member having a first end and a second end and a deployable heart-engaging assembly connected to at least the first end. The method includes advancing the elongate member through vasculature structure and into the heart chamber such that the first end of the elongate member extends through a first location of a wall surrounding the heart chamber and the second end extends through a second location of the heart chamber wall substantially opposite the first location. A deployable heart-engaging assembly is deployed such that it engages with a first exterior surface portion of the heart chamber wall adjacent the first location. The elongate member is secured with respect to the heart with a second heart-engaging assembly connected to the second end. The second heart-engaging assembly engages with a second exterior surface portion of the heart chamber wall adjacent the second location. A splint assembly includes an expandable heart-engaging assembly formed partially from portions forming the elongate member of the splint assembly. A delivery tool includes a tubular member configured to be advanced through vasculature structure and has a curved distal end.

25 Claims, 25 Drawing Sheets

U.S. PATENT DOCUMENTS

| | | |
|---|---|---|
| 6,095,968 A | 8/2000 | Snyders |
| 6,102,944 A | 8/2000 | Huynh et al. |
| 6,143,025 A | 11/2000 | Stobie et al. |
| 6,174,279 B1 | 1/2001 | Girard |
| 6,179,791 B1 | 1/2001 | Krueger |
| 6,182,664 B1 | 2/2001 | Cosgrove |
| 6,183,512 B1 | 2/2001 | Howanec, Jr. et al. |
| 6,190,408 B1 | 2/2001 | Melvin |
| 6,193,648 B1 | 2/2001 | Krueger |
| 6,197,053 B1 | 3/2001 | Cosgrove et al. |
| 6,206,820 B1 | 3/2001 | Kazi et al. |
| 6,217,610 B1 | 4/2001 | Carpentier et al. |
| 6,221,103 B1 | 4/2001 | Melvin |
| 6,221,104 B1 | 4/2001 | Buckberg et al. |
| 6,224,540 B1 | 5/2001 | Lederman et al. |
| 6,230,714 B1 | 5/2001 | Alferness et al. |
| 6,231,602 B1 | 5/2001 | Carpentier et al. |
| 6,238,334 B1 | 5/2001 | Easterbrook, III et al. |
| 6,241,654 B1 | 6/2001 | Alferness |
| 6,245,105 B1 | 6/2001 | Nguyen et al. |
| 6,250,308 B1 | 6/2001 | Cox |
| 6,258,021 B1 | 7/2001 | Wilk |
| 6,269,819 B1 | 8/2001 | Oz et al. |
| 6,283,993 B1 | 9/2001 | Cosgrove et al. |
| 6,293,906 B1 | 9/2001 | Vanden Hoek et al. |
| 6,312,447 B1 | 11/2001 | Grimes |
| 6,314,322 B1 | 11/2001 | Rosenberg |
| 6,332,893 B1 | 12/2001 | Mortier et al. |
| 6,343,605 B1 | 2/2002 | Lafontaine |
| 2001/0003986 A1 | 6/2001 | Cosgrove |
| 2001/0014811 A1 | 8/2001 | Hussein |
| 2001/0018611 A1 | 8/2001 | Solem et al. |
| 2001/0029314 A1 | 10/2001 | Alferness et al. |
| 2001/0034551 A1 | 10/2001 | Cox |
| 2001/0041821 A1 | 11/2001 | Wilk |
| 2001/0044568 A1 | 11/2001 | Langberg et al. |
| 2001/0047122 A1 | 11/2001 | Vanden Hoek et al. |
| 2002/0007216 A1 | 1/2002 | Melvin |
| 2002/0013571 A1 | 1/2002 | Goldfarb et al. |

FOREIGN PATENT DOCUMENTS

| | | |
|---|---|---|
| WO | 99/00059 | 1/1999 |
| WO | 99/52470 | 10/1999 |
| WO | 00/03759 | 1/2000 |
| WO | 00/06026 | 2/2000 |
| WO | 00/06028 | 2/2000 |
| WO | 00/27304 | 5/2000 |
| WO | 00/42950 | 7/2000 |
| WO | 00/42951 | 7/2000 |
| WO | 00/60995 | 10/2000 |
| WO | 00/61033 | 10/2000 |
| WO | 00/62715 | 10/2000 |
| WO | 01/00111 | 1/2001 |
| WO | 01/03608 | 1/2001 |
| WO | 01/19291 | 3/2001 |
| WO | 01/19292 | 3/2001 |
| WO | 01/21070 | 3/2001 |
| WO | 01/21098 | 3/2001 |
| WO | 01/21099 | 3/2001 |
| WO | 01/26557 | 4/2001 |
| WO | 01/28432 | 4/2001 |
| WO | 01/50981 | 7/2001 |
| WO | 01/54618 | 8/2001 |
| WO | 01/54745 | 8/2001 |
| WO | 01/67985 | 9/2001 |
| WO | 01/85061 | 11/2001 |
| WO | 01/91667 | 12/2001 |
| WO | 01/95830 | 12/2001 |
| WO | 01/95831 | 12/2001 |
| WO | 01/95832 | 12/2001 |

OTHER PUBLICATIONS

Melvin, DB, "Ventricular Radius–Reduction Without Resection, A Computational Assessment", undated.

Melvin et al., "Reduction of Ventricular Wall Tensile Stress by Geometric Remodeling Device," 1 page, undated.

Melvin, DB et al., "Reduction of Ventricular Wall Tensile Stress by Geometric Remodeling Device," Poster Text, ASAIO, 1999.

Kay et al., "Surgical Treatment of Mitral Insufficiency", *The Journal of Thoracic Surgery*, 29: 618–620, 1955.

Harken et al., "The Surgical Correction of Mitral Insufficiency", *The Journal of Thoracic Surgery*, 28:604–627, 1954.

Bailey et al., "Closed Intracardiac Tactile Surgery", *Diseases of the Chest*, XXII:1–24, Jul./1952.

Sakakibara, "A Surgical Approach to the Correction of Mitral Insufficiency", *Annals of Surgery*, 142:196–203, 1955.

Glenn et al., "The Surgical Treatment of Mitral Insufficiency: The Fate of A Vascularized Transchamber Intracardiac Graft", *Annals of Surgery*, 141:510–518, Apr./1995.

Kay et al., "Surgical Treatment of Mitral Insufficiency", *Surgery*, 37:697–706, May/1955.

Bailey et al. "The Surgical Correction of Mitral Insufficiency By The Use of Pericardial Grafts", *The Journal of Thoracic Surgery*, 28:551–603, Dec./1954.

Harken et al., "The Surgical Correction of Mitral Insufficiency", Surgical forum, 4:4–7, 1953.

Shumacker, Jr., "Attempts to Control Mitral Regurgitation", *The Evolution of Cardiac Surgery*, 203–210, 1992.

ENDOVASCULAR SPLINTING DEVICES AND METHODS

FIELD OF THE INVENTION

The present invention pertains to devices for treating a failing heart and related methods for placing the devices. In particular, the invention pertains to splinting devices placed on the heart to reduce the radius of curvature and/or alter the geometry or shape of the heart to thereby reduce wall stress in the heart and improve the heart's pumping performance. The devices and methods of the present invention are directed toward endovascular techniques used to facilitate placement of the splinting devices on the heart.

BACKGROUND OF THE INVENTION

Heart failure is a common outcome in the progression of many forms of heart disease. Heart failure may be considered as the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure. Typically these processes result in dilatation of the left ventricular chamber. Etiologies that can lead to this form of failure include idiopathic, valvular, viral, and ischemic cardiomyopathies, including ventricular aneurysms.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased it requirements put on the contracting myocardium to such a level that this compensated state is never achieved and the heart continues to dilate.

One problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress also occurs during diastolic filling. Additionally, because of the lack of cardiac output, a rise in ventricular filling pressure generally results from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Mitral regurgitation is a condition whereby blood leaks through the mitral valve due to an improper positioning of the valve structures that causes the valve not to close entirely. Geometric abnormalities resulting from a dilated left ventricle may cause or exacerbate improper functioning of the mitral valve, including mitral valve regurgitation, by altering the normal position and dimension of the valve, particularly the Valve annulus.

Prior treatments for heart failure associated with such dilatation fall into three general categories. The first being pharmacological, for example, diuretics and ACE inhibitors. The second being assist systems, for example, pumps. Finally, surgical treatments also have been experimented with.

With respect to pharmacological treatments, diuretics have been used to reduce the workload of the heart by reducing blood volume and preload. Diuretics typically reduce extra cellular fluid which builds in congestive heart failure patients increasing preload conditions. Nitrates, arteriolar vasodilators, angiotensin converting enzyme (ACE) inhibitors have been used to treat heart failure through the reduction of cardiac workload by reducing afterload. Inotropes function to increase cardiac output by increasing the force and speed of cardiac muscle contraction. These drug therapies offer some beneficial effects but do not stop the progression of the disease.

Assist devices include mechanical pumps. Mechanical pumps reduce the load on the heart by performing all or part of the pumping function normally done by the heart. Currently, mechanical pumps are used to sustain the patient while a donor heart for transplantation becomes available for the patient.

There are at least four surgical procedures for treatment of heart failure associated with dilatation: 1) heart transplantation; 2) dynamic cardiomyoplasty; and 3) the Batista partial left ventriculectomy, and 4) the Jatene and Dor procedures for ischemic cardiomyopathy. These procedures are set forth in slightly more detail in U.S. application Ser. No. 09/532,049, filed Mar. 21, 2000, entitled "Splint Assembly for Improving Cardiac Function in Hearts, and Method for Implanting the Splint Assembly," the entire disclosure of which is hereby incorporated by reference herein. Hereinafter, this application will be referred to as "the '049 application."

SUMMARY OF THE INVENTION

Due to the drawbacks and limitations of the previous devices and techniques for treating a failing heart, including such a heart having dilated, infarcted, and/or aneurysmal tissue, there exists a need for alternative methods and devices that are less invasive and pose less risk to the patient, both after and during placement, and are likely to possess more clinical utility.

Thus, a more recent procedure for treating the various forms of heart failure discussed above includes placing devices on the heart to reduce the radius of curvature of the heart and/or alter the cross-sectional shape of the heart to reduce wall stress. The devices are configured to reduce the tension in the heart wall, and thereby reverse, stop or slow the disease process of a failing heart as it reduces the energy consumption of the failing heart, decreases isovolumetric contraction, increases isotonic contraction (sarcomere shortening), which in turn increases stroke volume. The devices reduce wall tension by changing chamber geometry or shape and/or changing the radius of curvature or cross-section of a heart chamber. These changes may occur during the entire cardiac cycle or during only a portion of the cardiac cycle. The devices of the present invention which reduce heart wall stress in this way can be referred to generally as "splints." These splints can be in the form of external devices, as described in U.S. application Ser. No. 09/157,486, filed Sep. 21, 1998, entitled "External Stress Reduction Device and Method," the entire disclosure of which is incorporated by reference herein, or in the form of transventricular elongate tension members with heart-engaging assemblies, typically in the form of anchor pads, disposed on each end configured to engage substantially opposite portions of the chamber wall, embodiments of which are disclosed in the '049 application incorporated above.

An aspect of the present invention pertains to splint devices, and related splinting methods, for endovascular implantation on the heart. The splints of the present invention may be implanted endovascularly through remote vascular access sites. The inventive techniques and devices thus are minimally invasive and less risky to patients.

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

According to an aspect of the invention, a method for placing a splint assembly transverse a heart chamber comprises providing an elongate member having a first end and a second end and a deployable heart-engaging assembly connected to at least the first end. The method further includes advancing the elongate member through vasculature structure and into the heart chamber such that the first end of the elongate member extends through a first location of a wall surrounding the heart chamber and the second end extends through a second location of the heart chamber wall substantially opposite the first location. A deployable heart-engaging assembly is deployed such that it engages with a first exterior surface portion of the heart chamber wall adjacent the first location. The elongate member is secured with respect to the heart with a second heart-engaging assembly connected to the second end. The second heart-engaging assembly engages with a second exterior surface portion of the heart chamber wall adjacent the second location.

Another aspect of the invention includes a splint assembly for treating a heart, comprising an elongate member configured to extend transverse a chamber of the heart and at least one heart-engaging assembly formed at least partially from portions forming the elongate member. The heart-engaging assembly has a collapsed configuration adapted to travel through a heart wall and an expanded configuration adapted to engage the heart wall.

Yet another aspect of the invention includes a delivery tool for delivering a transventricular splint assembly to a chamber of the heart, comprising a tubular member having a distal end and a proximal end, the distal end having a curved configuration and the tube defining a lumen configured to carry at least a portion of the splint assembly. The delivery tool further includes at least one support mechanism disposed proximate the distal end of the tubular member, the support mechanism being configured to stabilize the tubular member with respect to a heart wall surrounding the chamber. The tubular member is configured to be advanced through vasculature structure and into the heart chamber.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DETAILED DESCRIPTION OF THE PREFERRED EMBODIMENTS

Figure 2:
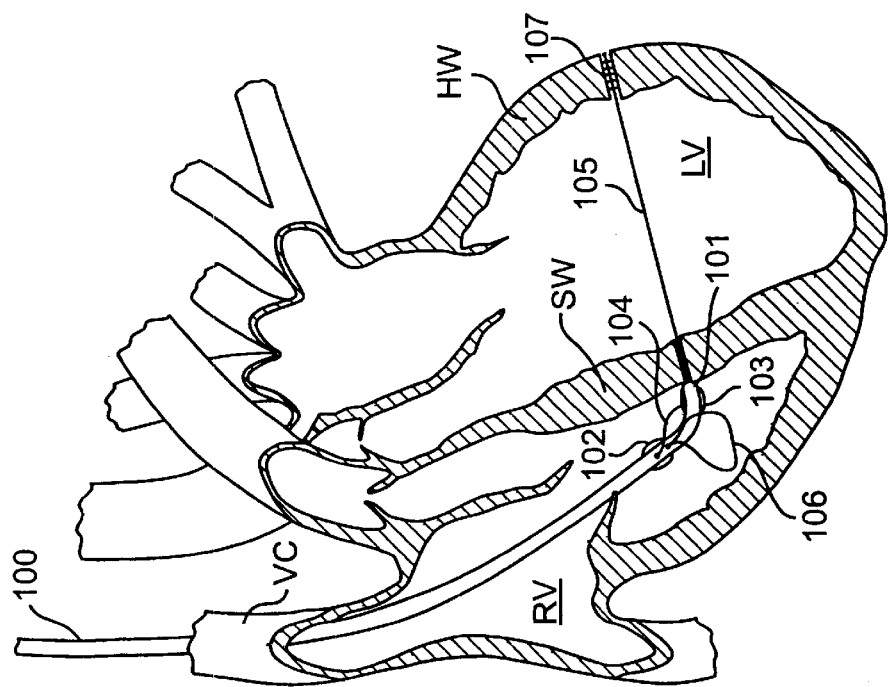
FIG. 2 is a vertical cross-sectional view of the heart showing a guide wire extending from the catheter of FIG. 1 through the septal wall, across the left ventricular chamber and into the free wall according to an aspect of the present invention.

The various aspects of the invention to be discussed herein generally pertain to devices and methods for treating heart conditions, including, for example, dilatation, valve incompetencies, including mitral valve leakage, and other similar heart failure conditions. Each device of the present invention preferably operates passively in that, once placed in the heart, it does not require an active stimulus, either mechanical, electrical, or otherwise, to function. Implanting one or more of these devices alters the shape or geometry of the heart, both locally and globally, and thereby increases the heart's efficiency. That is, the heart experiences an increased pumping efficiency through an alteration in its shape or geometry and concomitant reduction in stress on the heart walls. In addition, the devices of the present invention may operate to assist in the apposition of heart valve leaflets to improve valve function.

The inventive devices and related methods offer numerous advantages over the existing treatments for various heart conditions, including valve incompetencies. The devices are relatively easy to manufacture and use, and the surgical techniques and tools for implanting the devices of the present invention do not require the invasive procedures of current surgical techniques. For instance, the endovascular techniques which will be described do not require performing a sternotomy or removing portions of the heart tissue, nor do they require opening the heart chamber or stopping the heart during operation. Such percutaneous insertion permits the splinting procedures to be performed in a wide variety of laboratories in the hospital. For these reasons, the techniques for implanting the devices of the present invention also are less risky to the patient, both during and after the implantation, and may be performed more quickly than other techniques. For instance, the procedures of the invention cause less pain to patients and permit quicker healing. In addition, certain endovascular splinting techniques to be described may limit bleeding at access sites, allowing relatively large catheters, cannula, and other similar implantation tools to be inserted in a percutaneous manner.

The disclosed inventive devices and related methods involve geometric reshaping of the heart. In certain aspects of the inventive devices and related methods, substantially the entire chamber geometry is altered to return the heart to a more normal state of stress. Models of this geometric reshaping, which includes a reduction in radius of curvature of the chamber walls, can be found in U.S. Pat. No. 5,961,440, issued Oct. 5, 1999, entitled "Heart Wall Tension Reduction Apparatus and Method," and incorporated by reference herein. Prior to reshaping the chamber geometry, the heart walls experience high stress due to a combination of both the relatively large increased diameter of the chamber and the thinning of the chamber wall. Filling pressures and systolic pressures are typically high as well, further increasing wall stress. Geometric reshaping according to the present invention reduces the stress in the walls of the heart chamber to increase the heart's pumping efficiency, as well as to stop further dilatation of the heart.

It also is contemplated that the inventive endovascular splinting devices and methods will be used to support an infarcted heart wall to prevent further dilatation, or to treat aneurysms in the heart. U.S. application Ser. No. 09/422,328, filed on Oct. 21, 1999, entitled "Methods and Devices for Improving Cardiac Function in Hearts," which is assigned to the same assignee as the present application and is incorporated by reference herein, discusses this form of heart failure in more detail. Moreover, it is contemplated that the devices and methods of using and implanting the devices could be used to treat heart valves, for example to aid in apposition of the leaflets of a mitral valve or modify the shape of the mitral valve, as described in U.S. application Ser. No. 09/680,435, to Richard F. Schroeder et al., filed on the same day as this application, assigned to the same assignee as the present application, and entitled "Methods and Devices for Improving Mitral Valve Function," and incorporated by reference herein. One of ordinary skill in the art would understand that the use of the devices and methods described herein also could be employed in other chambers and for other valves associated with those chambers. For example, the devices and methods of the invention might be used to reduce stress in the left atrium to treat atrial fibrillation. The left ventricle has been selected for illustrative purposes because a large number of the disorders that the present invention treats occur in the left ventricle.

Reference will now be made in detail to the present preferred embodiments of the invention, examples of which are illustrated in the accompanying drawings. Wherever possible, the same reference numbers will be used throughout the drawings to refer to the same or like parts.

An embodiment of an endovascular splinting technique according to the present invention is shown in FIGS. 1–10. In this splinting technique, access to the left ventricle LV and delivery of the splint occurs from within the right ventricle RV. An approach from within the right ventricle is preferred for a number of reasons. First, the right ventricle is highly accessible through venous structure that leads into the superior vena cava VC, for example from the right or left jugular veins. Since these veins typically are at a relatively low pressure, bleeding at the access sites is limited, and rather large catheters, cannula and the other like surgical tools can be inserted into the veins in a percutaneous manner. Furthermore, this technique permits access to vascular structure without a sternotomy or other open chest surgical access, thereby minimizing trauma to the patient. Additionally, patients are less likely to experience embolic events. Recovery times for the operation also are reduced, due to the minimally invasive nature of such procedures.

Second, delivery through the right ventricle allows for straightforward positioning of the splints on the ventricular septal wall SW. Such positioning on the septal wall is preferable because it results in good left ventricle bisection, in a manner believed to have minimal negative impact on mitral valve function, and in some instances, a positive impact on mitral valve function and performance. Moreover, delivery through it the right ventricle does not involve the free wall of the right ventricle and also does not restrict outflow of the blood from the heart.

Figure 1:
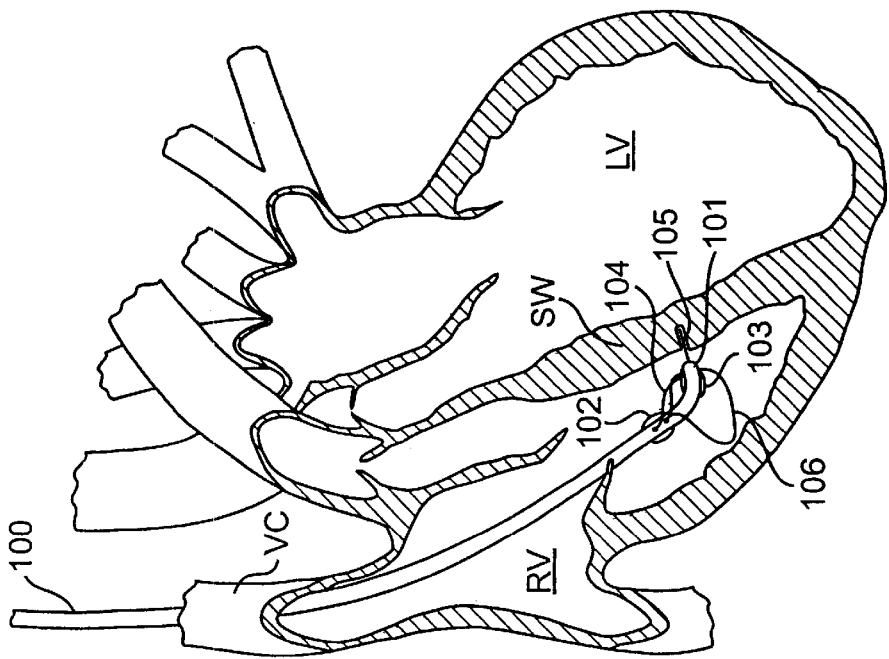
FIG. 1 is a vertical cross-sectional view of the heart showing a delivery catheter inserted endovascularly into the right ventricule according to an aspect of the present invention.
Figure 23:
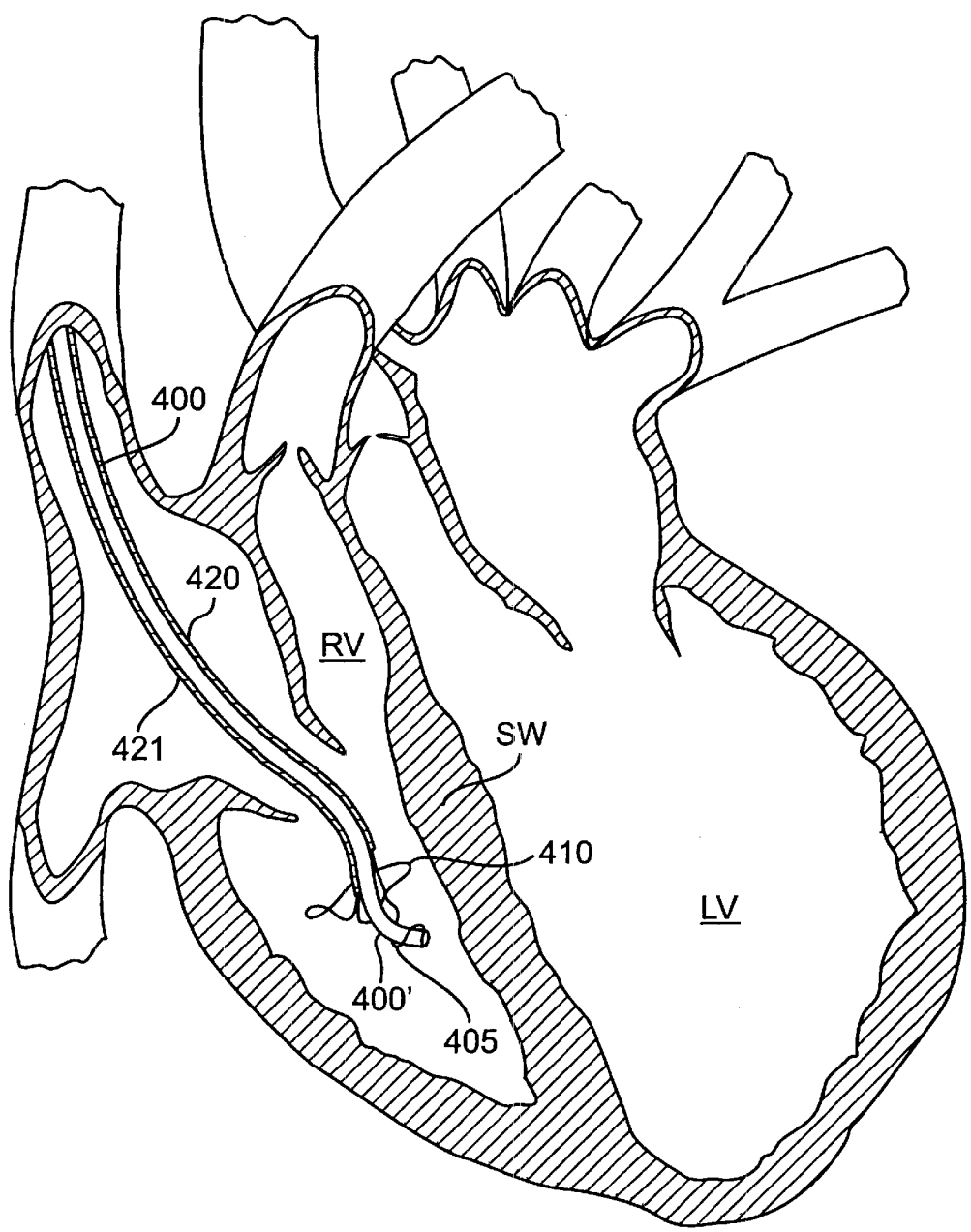
FIG. 23 is a vertical cross-sectional view of the heart showing a delivery catheter with a curved distal tip inserted into the right ventricle proximate the septal wall for delivering a splint assembly according to an aspect of the present invention.

According to the right ventricle delivery technique shown in FIGS. 1–10, a shaped guide device in the form of a delivery catheter 100 is advanced into right ventricle RV from an access site preferably in the left or right jugular vein. Other access sites, such as, for example, the left or right subclavian vein also are contemplated. As shown in FIG. 1, the catheter 100 has a tip portion 101 configured to be adjustably and variably curved through the use of an adjusting pull-wire 104. The pull-wire 104 attaches to the distal most end of the catheter, has a portion that extends exterior the catheter at the distal end of the catheter, and then extends through the catheter to a proximal end of the catheter where it is controlled. As shown in FIGS. 1 and 2, pull wire 104 may be an essentially straight wire that, when pulled (or tensioned), causes tip portion 101 to curve. In another embodiment, a pull wire may take the form of a tether, such as described below with reference to the curved catheter having pull wire 405 in FIG. 23. Also in that embodiment, the proximal end of the pull-wire 405 can be pulled and released to thereby cause the distal tip of the catheter to curve and to straighten as desired. Thus, the position of the catheter tip can be curved by adjusting the pull-wire and also advanced or rotated, or both, by advancing or rotating the catheter with respect to the right ventricle and septal wall.

Figure 16:
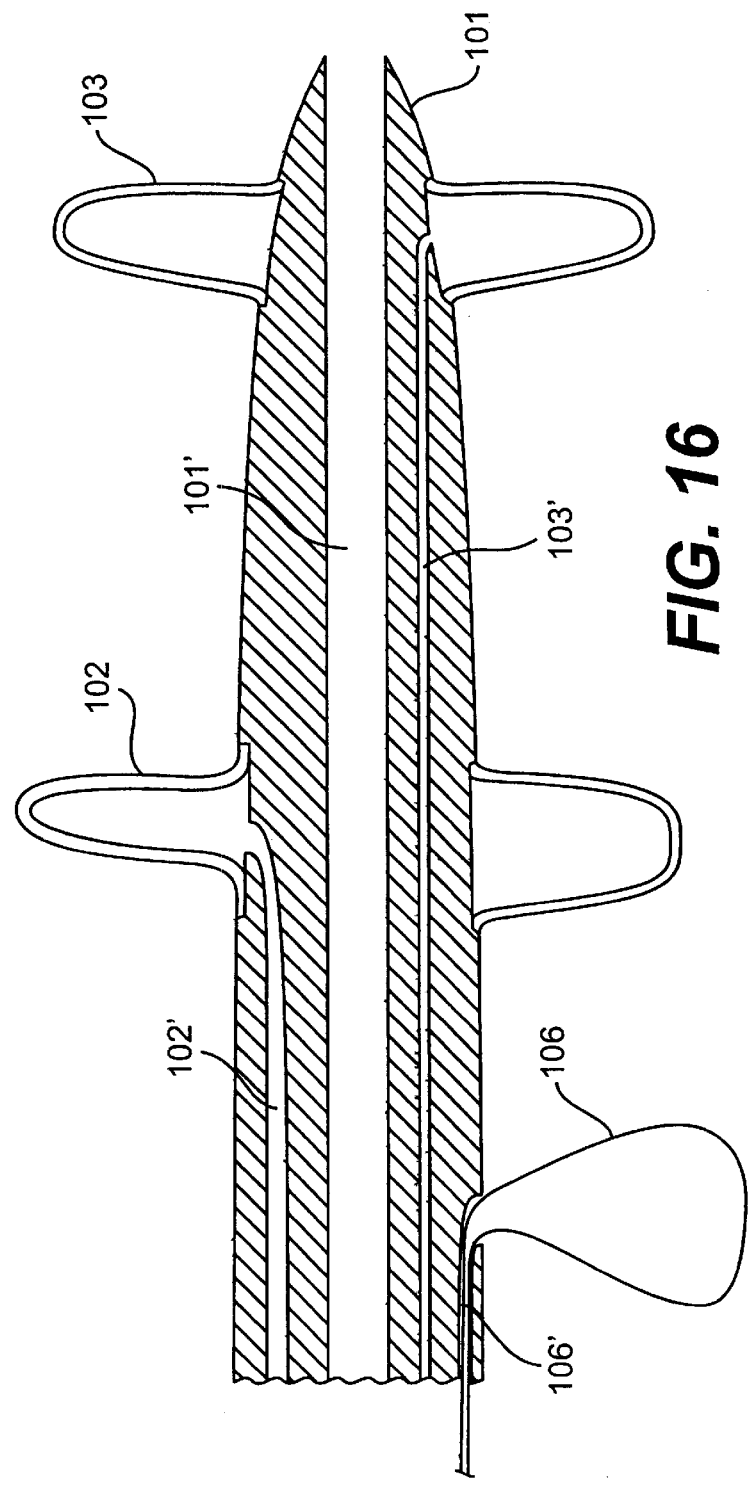
FIG. 16 is a detailed, partial side cross-sectional view of the delivery catheter of FIGS. 1–6 according to an aspect of the present invention.

Additionally, as shown best in FIG. 16, two anchoring balloons 102, 103 are disposed near the distal end of catheter 100. Each balloon 102, 103 is in fluid communication with a corresponding inflation lumen 102', 103' that extends proximally to an inflating means (not shown). A lumen 101' configured to carry a piercing needle also extends through the length of catheter 100. In a preferred embodiment, delivery catheter 100 additionally defines a lumen 106' for carrying a preformed support wire 106, which expands upon advancement of support wire 106 relative to catheter 100. The wire 106 takes on a hoop-like shape which gives mechanical "back up" support to delivery catheter 100. The support wire 106 also helps to position the catheter 100 within the right ventricle to allow for positioning within the right ventricle RV and with respect to the septal wall SW.

The support wire 106 is preferably made from an elastic material, such as a nickel-titanium alloy or the like, and has a preformed shape at or near a distal end of the wire configured to stabilize and position the catheter 100. The catheter 100 preferably also includes radiographic and echogenic markers (not shown), such as metallic or gas-filled structures, or relatively small balloons filled with a contrast media, to facilitate positioning of the catheter under fluoroscopic and/or ultrasonic guidance, such as transesophageal echo (TEE).

Figure 15:
FIG. 15 is a close-up, partial side view of the guidewire of FIG. 2 according to an aspect of the present invention.

Once catheter 100 is manipulated to a desired position on the ventricular septum; SW, the support wire 106 is advanced to stabilize the tip position, as shown in FIG. 1. A sharpened needle, or guidewire,105 is then advanced through the lumen in catheter 100 and out of tip portion 101, piercing the septal wall SW, and extending across the left ventricle chamber LV. Preferably, needle 105 is fabricated of a highly elastic material such as, for example, nickel titanium alloy, which will allow the needle to traverse the bend at the tip of the delivery catheter, and then to straighten out for controlled traversing across left ventricle LV. FIG. 15 shows the distal portion of needle 105 in greater detail. As can be seen from this figure, needle 105 includes a sharpened tip which may have threads 107 disposed around the outer surface of the tip portion. These threads 107 preferably are flexible such that they can lay substantially flat along the length of needle 105 as the needle traverses through the catheter lumen. Alternatively, the tip may include barbs or other similar structures that aid in anchoring the tip in the heart wall.

Once needle 105 is across the left ventricle chamber, its position is confirmed by TEE, X-Ray, or other visualization techniques, to assure good bisection and avoidance of key mitral valve and other heart structure. Conventional angiography utilizing a "pigtail" catheter. i.e., a dye injection catheter with a loop shape at the distal end, in the left ventricle LV and angiography catheters in one or both coronary artery ostia may also be used to aid in proper positioning of the associated delivery devices in the LV. It also is important to assure that needle 105 will not penetrate or damage any significant coronary vasculature. To assure this, an angiogram may be performed. Preferably, the angiographic image is aligned to a position that looks down the axis of the needle in the portion of the needle which traverses the left ventricle LV. This angle will limit parallax to ensure that if the tip of the needle is not coincident with a significant vessel it will not pierce such vessel. Any small variation in the position of the needle tip can be adjusted by gentle manipulation of the delivery catheter.

As mentioned above, preferably needle 105 has soft threads 107 disposed on the surface of a tip portion of the needle, as shown in FIG. 15. Needle 105 can be advanced into the free wall HW of the left ventricle LV by rotating the needle, essentially causing the tip portion of the needle to be pulled or screwed into the myocardium. Threads 107 also serve to anchor needle 105 and provide support for the further advancement of delivery catheter 100.

Figure 3:
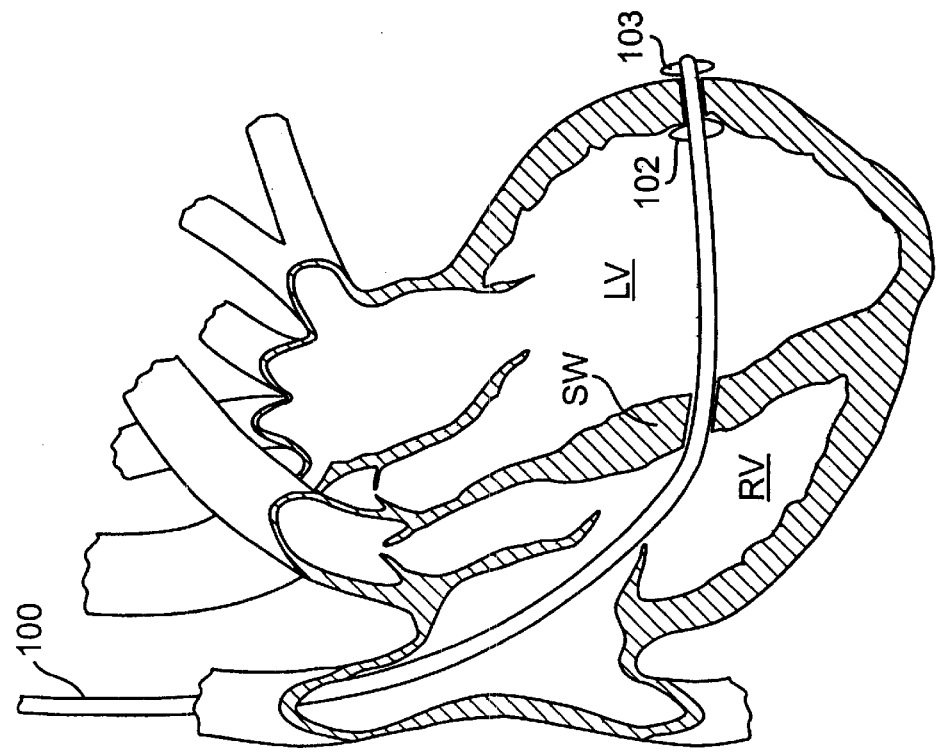
FIG. 3 is a vertical cross-sectional view of the heart showing the deliver catheter of FIG. 1 positioned over the guidewire of FIG. 2 with positioning balloons inflated on either side of the free wall according to an aspect of the present invention.

Next, delivery catheter 100 is straightened and advanced over needle 105 into left ventricle LV. A tapered tip 101 on delivery catheter 100 enables catheter 100 to penetrate the septal and free walls SW, HW. Once distal anchoring balloon 103 traverses across the free wall HW, both balloons 102 and 103 are inflated, as shown in FIG. 3, to stabilize catheter 100 with respect to the heart chamber. Preferably, these balloons 102, 103 are made of an elastomeric material, such as latex or silicone, for example, to provide a relatively low profile in the non-inflated state. Thus, once inflated with, for example, air or other fluid, including a radiographic contrast agent, balloons 102, 103 preferably have a flattened, "pancake" shape. This shape may be particularly important for distal balloon 103, as it lies in the space between the outside of the myocardium and the pericardial sac. To further guard against damage to the pericardium or lungs, it is possible to insufflate the space between the myocardium and the pericardial sac with $CO_2$. Insufflation can occur with the use of a small lumen provided inside needle 105. Once needle 105 is across the myocardium, the $CO_2$ can be infused.

Figure 4:
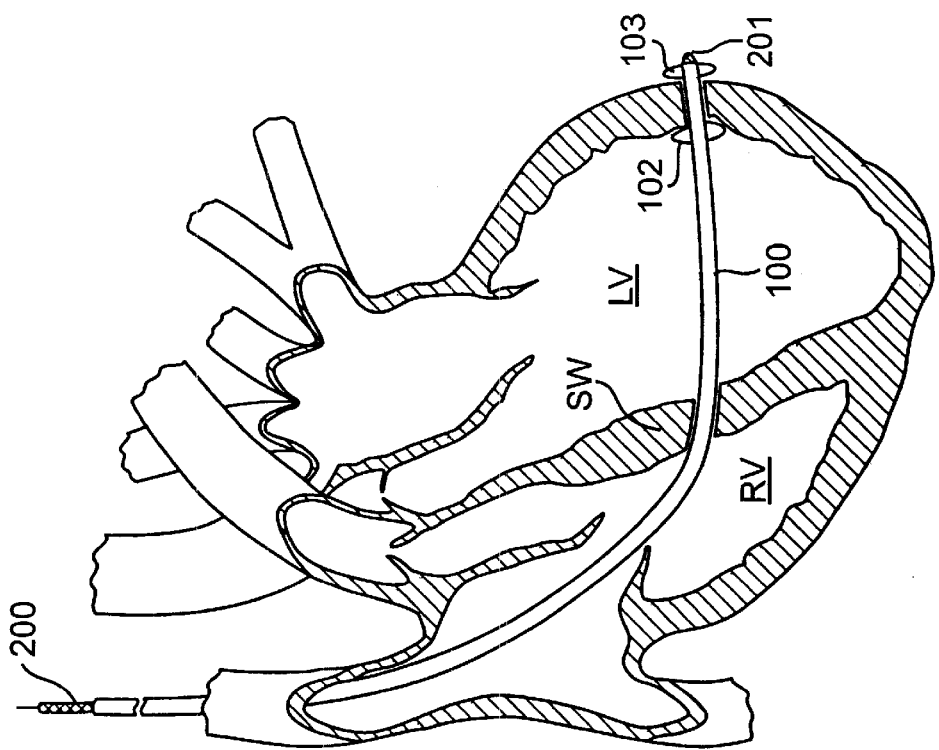
FIG. 4 is a vertical cross-sectional view of the heart showing the insertion of a tension member into the delivery catheter of FIG. 3 for placement with respect to the left ventricle according to an aspect of the present invention.

As delivery catheter 100 is advanced over the distal end of needle 105, flexible threads 107 become collapsed and needle 105 can be removed from catheter 100. After removing needle 105, an elongate tension member 200 with a heart-engaging assembly, preferably in the form of a collapsible fixed anchor mechanism 201(free wall anchor), on its distal end can be inserted into the lumen of catheter 100. Tension member 200 is advanced until it begins to emerge from the tip portion 101 of delivery catheter 100, as shown in FIG. 4.

Figure 11:
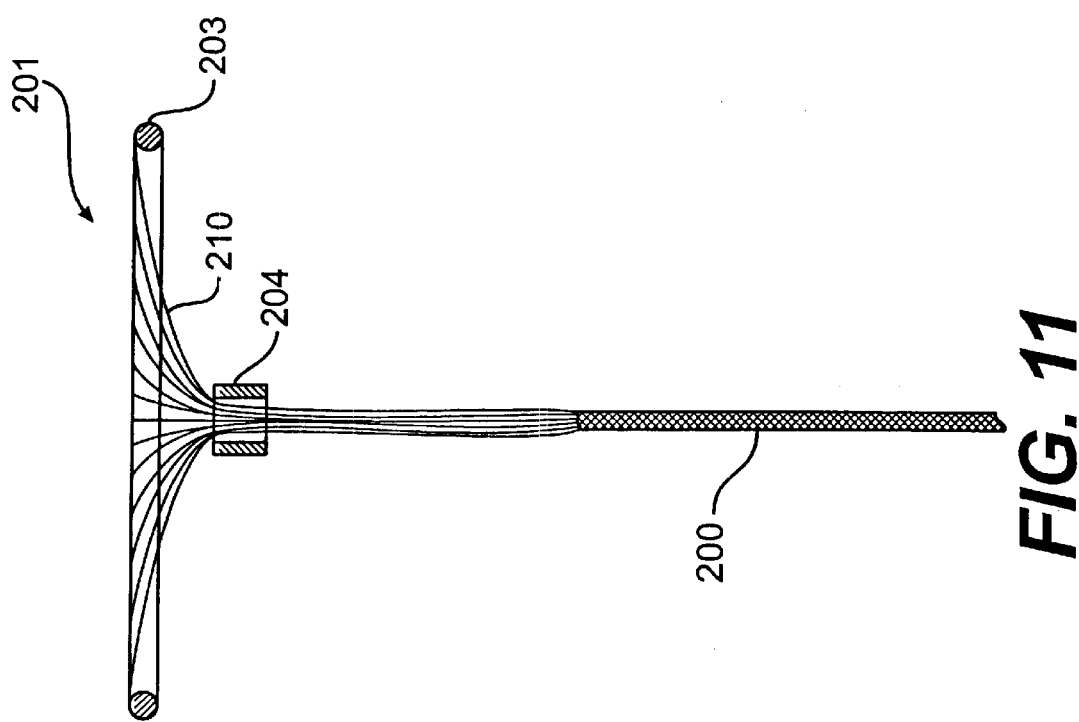
FIG. 11 is a partial side view of the deployable anchor and tension member of FIGS. 5 and 6 according to an aspect of the present invention.
Figure 13:
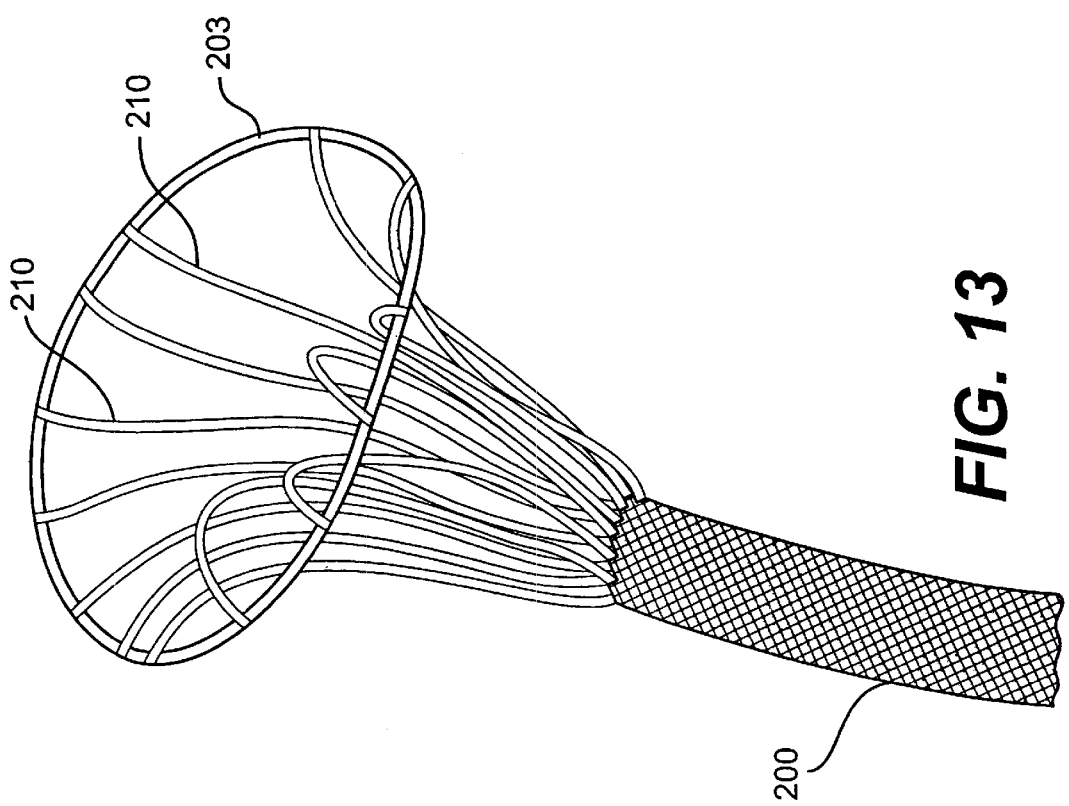
FIG. 13 is a partial perspective view of the deployable anchor and tension member of FIG. 11 prior to a securing band being placed to tighten the filament bundles on the elastic ring portion of the anchor according to an aspect of the invention.

FIG. 11 shows a preferred structure for fixed anchor mechanism 201 in its fully expanded state after being secured with respect to the heart wall. As shown, tension member 200 is comprised of a braided polymer, such as that disclosed in the '049 application incorporated by reference above. A cover of expanded polytetrafluoroethylene (ePTFE) (not shown) preferably covers the majority of the length of tension member 200. Each bundle 210 in the braid structure is attached via suturing, adhesive, or other suitable attachment mechanism, to a flexible elastic ring 203. Ring 203 preferably is comprised of nickel-titanium, or an elastomeric polymer such as silicone or urethane, or other suitable like materials. This attachment of the bundles to the ring is best shown in FIG. 13. In order to facilitate bundles 210 of the braid to be attached to ring 203, the braided structure transitions from a tight woven braid to a region that is primarily unbraided at a position slightly proximal to the ring.

In this configuration, flexible elastic ring 203 can be easily deformed into a flattened hoop, without bundles 210 inhibiting this deformation. This is the configuration that tension member 200 has as it is advanced through the lumen of delivery catheter 100. To allow tension member 200 to be pushed through catheter 100, a stiffening mandrel may be disposed either inside or adjacent the braided portion of the tension member.

Figure 5:
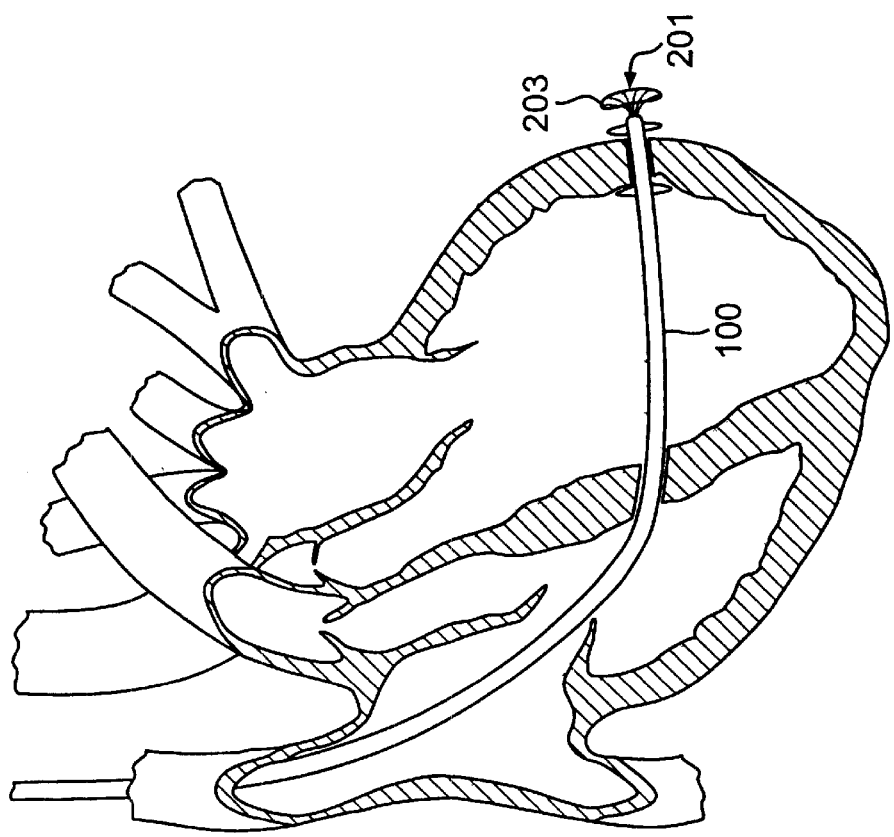
FIG. 5 is a vertical cross-sectional view of the heart showing a deployed fixed anchor on the distal end of the tension member of FIG. 4 after being extended past the distal end of the delivery catheter according to an aspect of the present invention.
Figure 12:
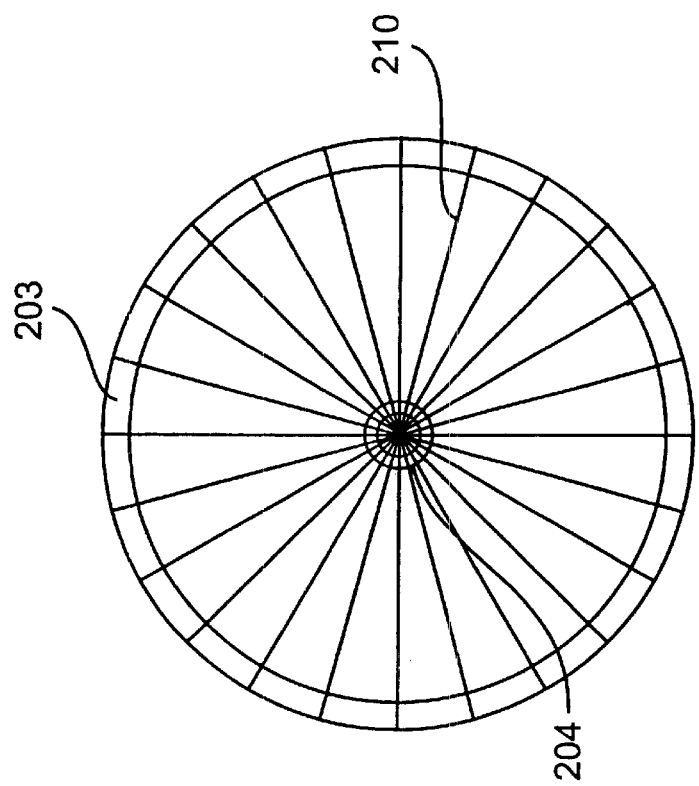
FIG. 12 is a top view of the anchor of FIG. 11 according to an aspect of the invention.
Figure 14:
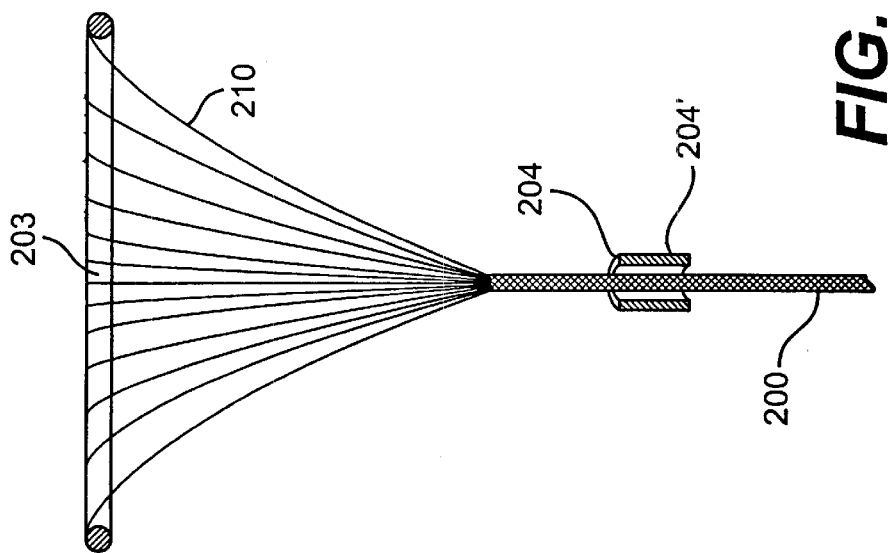
FIG. 14 is a partial side view of the anchor and tension member of FIG. 11 showing the placement of the securing/tightening band according to an aspect of the present invention.

As shown in FIG. 5, tension member 200 is advanced until flexible ring 203 fully emerges from the lumen of delivery catheter 100. As such, anchor mechanism 201 has sufficient strength to serve as an anchor and allows bundles 210 to take on a funnel shape, as shown in FIG. 13. To tighten fiber bundles 210, a securing band 204 (FIG. 14) is advanced along the outside of braided tension member 200, until the bundles tighten into a generally spoke-like configuration, as shown in FIGS. 11 and 12. A flexible pushing tube (not shown), or other suitable mechanism, may be used to advance securing band 204. Securing band 204 preferably has circumferential ribs 204' on its inner surface that are oriented proximally, as shown in FIG. 14. Ribs 204' allow for the band 204 to be advanced distally, while preventing proximal slipping. Once positioned, the securing band 204 maintains anchor mechanism 201 in a relatively flat profile, as shown in FIG. 11.

Figure 6:
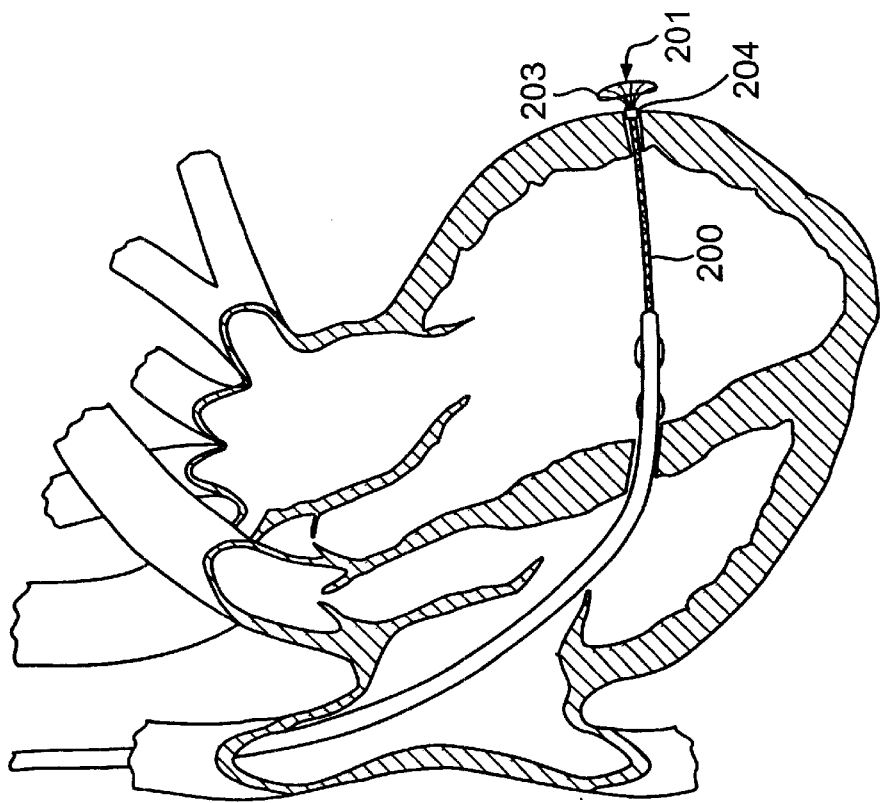
FIG. 6 is a vertical cross-sectional view of the heart showing the removal of the delivery catheter from the tension member of FIG. 5 according to an aspect of the present invention.

FIG. 6 shows tension member 200 and fixed anchor 201 in a fully deployed configuration with respect to the heart. After fixed anchor 201 of tension member 200 is deployed, anchor balloons 102,103 on delivery catheter 100 are deflated, and the delivery catheter is removed from tension member 200 and out of the heart.

Figure 7:
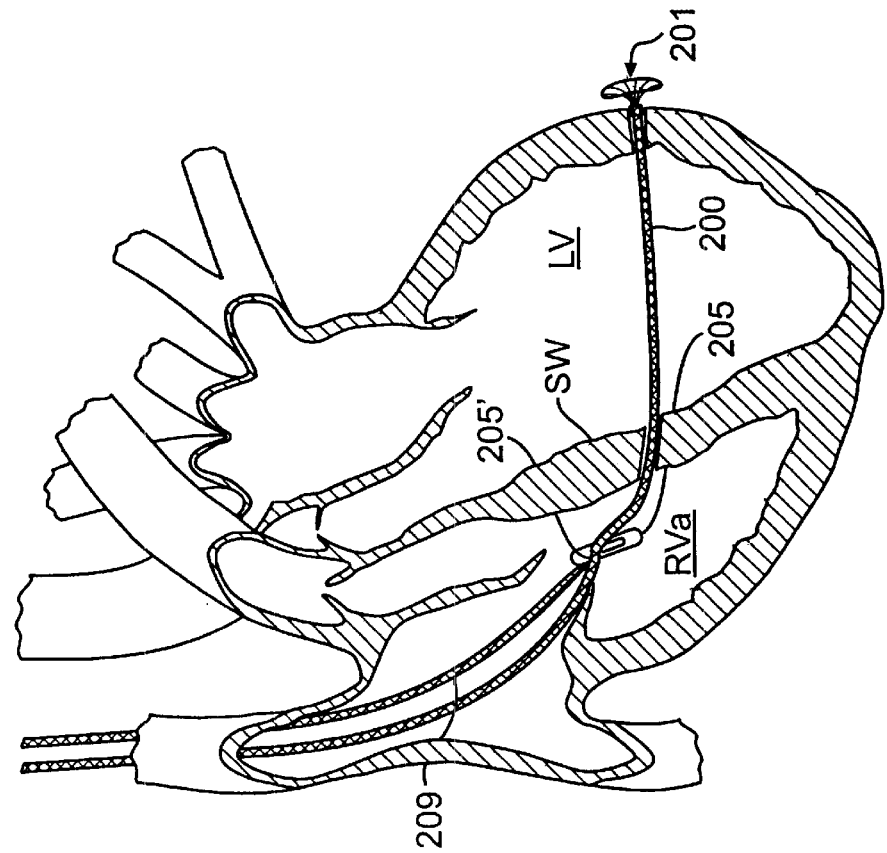
FIG. 7 is a vertical cross-section of the heart showing the delivery of an adjustable anchor to be placed on the tension member of FIG. 6 adjacent the septal wall according to an aspect of the present invention.

After removing delivery catheter 100, a second heart-engaging assembly, preferably in the form of an adjustable anchor pad 205 (septal wall anchor) is advanced over tension member 200 using a deployment tool 209, as shown in FIG. 7. Adjustable anchor pad 205 is similar in many ways to the adjustable pad assembly and deployment mechanism disclosed in the '049 application incorporated above, as will be explained. Thus, there preferably is an actuatable staple mechanism within the pad structure for securing pad 205 to braided tension member 200. In accordance with the present invention, however, pad 205 preferably has an oval, as opposed to circular, configuration. Such an oval configuration facilitates introduction of the pad into the access site in the vasculature. Moreover, a through hole 205' extending through this pad is angled relative to the pad surface, to allow pad 205 to be oriented in a more parallel fashion to the tension member 200 as it is advanced along the tension member 200, as shown in FIG. 7.

Adjustable pad 205 is advanced using deployment tool 209 over tension member 200 in essentially a "monorail" fashion, allowing anchor pad 205 to be oriented substantially adjacent and parallel to tension member 200 as tension member 200 slides through throughhole 205'. Once located at the septal wall SW, a tightening device 206, preferably in the form of a tube, is advanced over the outside of the tension member until the distal end of the tightening device 206 engages the adjustable pad 205. Manipulation of the tightening device 206 relative to tension member 200 positions adjustable pad 205 and tension member 200 into a position so as to alter the shape of the left ventricle LV.

Once a desired amount of shape change is achieved, adjustable pad 205 is deployed by manipulation of the deployment tool 209, in a manner similar to the technique disclosed in the '049 application. That is, the deployment tool 209 includes an actuator wire that is pre-engaged with an engagement collar (not shown) in adjustable pad assembly 205 such that when the actuator wire is pulled, the engagement collar travels through various channels disposed within the adjustable anchor pad 205. The engagement collar causes securement members, preferably in the form of pins or staples, such as staple 218 shown in FIG. 10, to move within the pad to engage with the braided tension member structure running through the pad. A more detailed description of the tightening of the splint assembly and the securing of the adjustable pad on the tension member can be found in the '049 application incorporated herein by reference.

Figure 9:
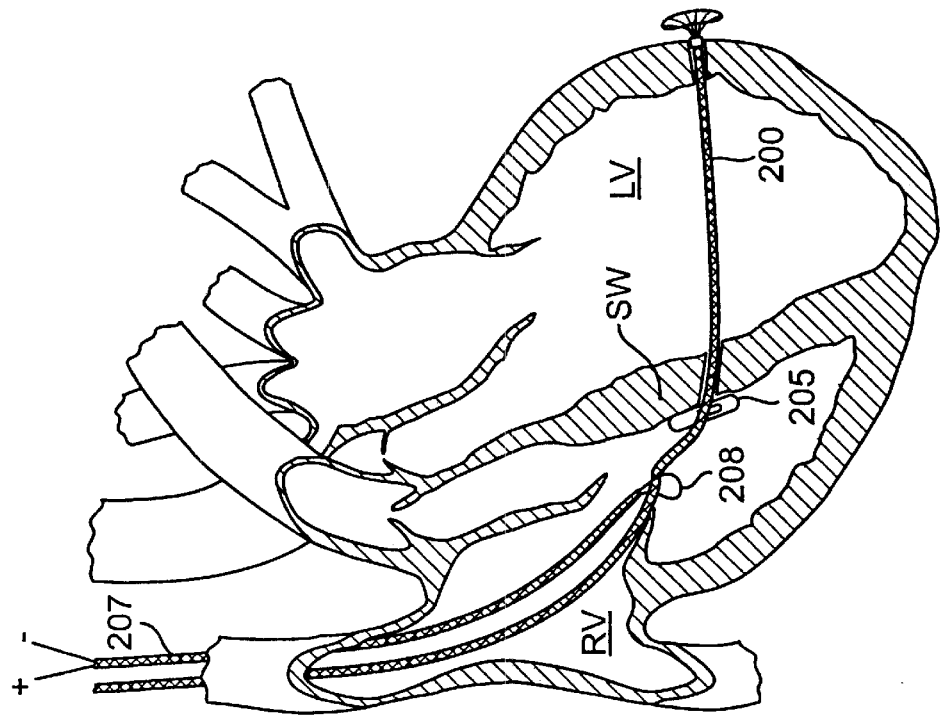
FIG. 9 is a vertical cross-section of the heart showing a cutting snare inserted into the right ventricle to cut excess tension member length from the splint assembly of FIG. 8 according to an aspect of the present invention.

FIG. 9 shows adjustable pad 205 secured onto tension member 200 adjacent septal wall SW within right ventricle RV after the tightening device 206 and the deployment tool 209 have been removed. A trimming catheter 207 containing a wire in a snare-like loop 208 is advanced along the excess length of tension member 200 to a position proximate the secured adjustable pad 205. Preferably, the wire forming snare like loop 208 can be heated such that upon retraction of snare loop 208 within the lumen of catheter 207, the excess length of tension member 200 is thermally severed and can be removed. The wire loop may also have a sharpened edge along its inside periphery to cut tension member 200 as loop 208 is retracted into catheter 207. Other suitable cutting mechanisms may be used and are contemplated as within the scope of the invention.

Figure 10:
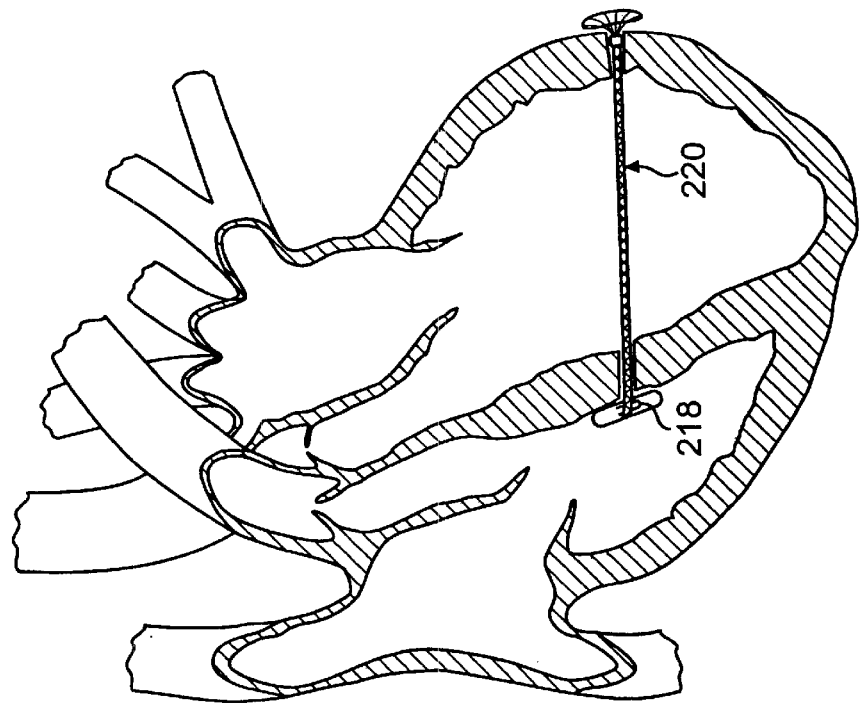
FIG. 10 is a vertical cross-section of the heart showing a splint assembly positioned with respect to the left ventricle according to an aspect of the present invention.
Figure 37:
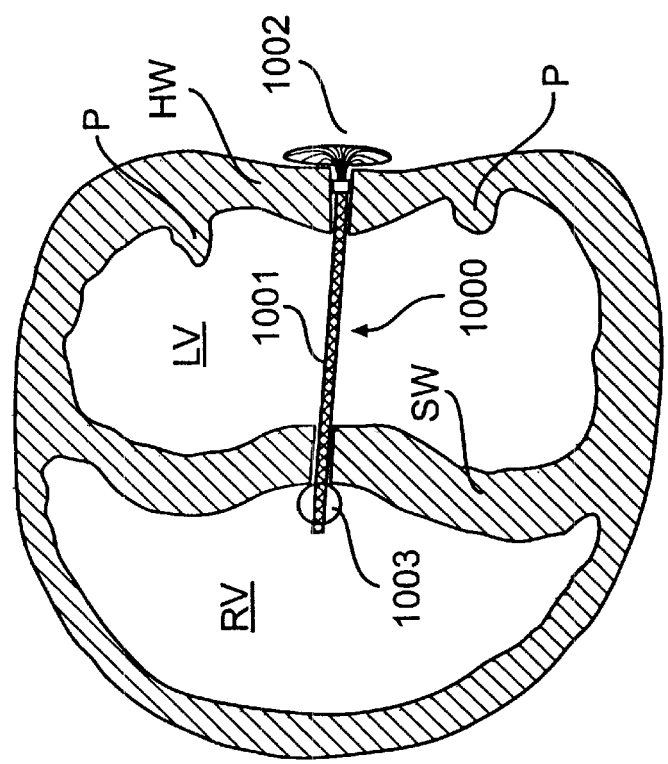
FIG. 37 is a transverse cross-sectional view of the heart showing a splint assembly placed with respect to the heart to treat a mitral valve according to an aspect of the present invention.

FIGS. 10 and 37 show fully deployed splints 220, 1000 in position with respect to the left ventricle LV of the heart.

Following the steps discussed above, additional splints may be positioned as needed or desired in the left ventricle LV or other chambers of the heart, including near the mitral valve to help improve valve function, as disclosed in the "Methods and Devices for Improving Valve Function" application filed on the same day as this application and incorporated by reference above. In a preferred method, three splints are positioned in a spaced, approximately parallel relationship from positions on the ventricular septum SW to positions on the ventricular free wall HW. Preferably, the splints are oriented perpendicular to the long axis of the left ventricle, as shown in FIGS. 10 and 37. Once all the desired splints are positioned, ii the access site in the vasculature is closed by conventional means, such as sutures and the like.

In another embodiment of the invention, splints can be positioned across the left ventricle via an endovascular route leading directly into the left ventricle rather than through the right ventricle. Using this approach, preferably the access site is located in one of the femoral arteries, in a manner similar to many cardiology procedures, for example. Although this route requires advancing delivery tools retrograde across the aortic valve, this delivery route permits the delivery catheter to be placed in approximately the middle of, rather than outside, the left ventricle, thus yielding a more symmetrical approach. The ability to position the splint to achieve a good bisection of the left ventricle therefore may be enhanced since the bisection may be easier to visualize prior to implanting the splints. Furthermore, it may be possible to stabilize the delivery system using walls on both sides of the left ventricle, thus requiring fewer additional support mechanisms.

Figure 17:
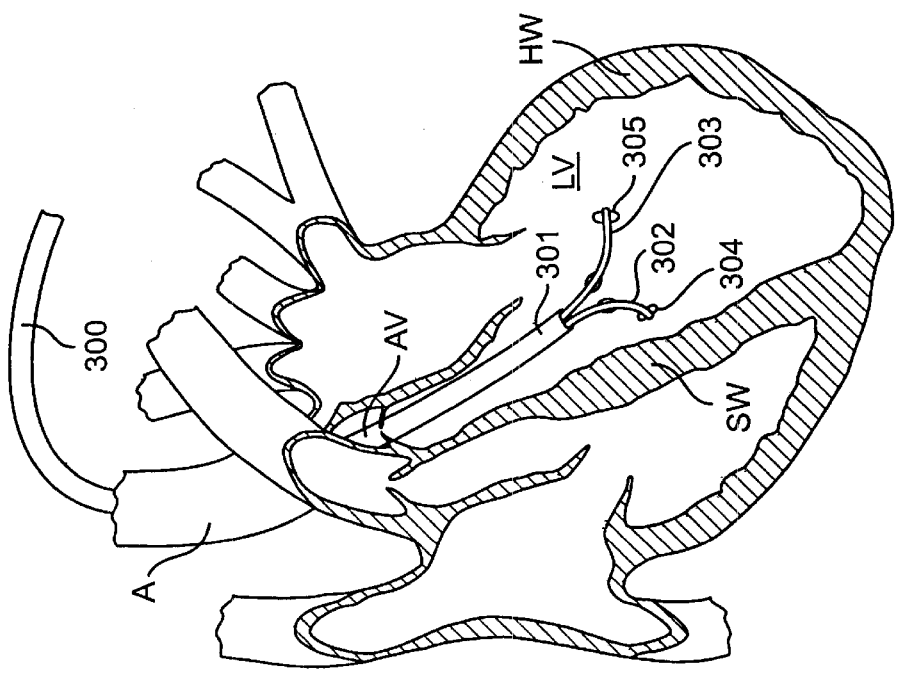
FIG. 17 is a vertical cross-sectional view of a heart showing a delivery catheter with two curved catheters inserted endovascularly through the aorta into the left ventricle according to an aspect of the present invention.

The direct left ventricle delivery approach uses a guide device, preferably in the form of a delivery catheter, of a different structure than that used in the right ventricle delivery approach. As shown in FIG. 17, a delivery catheter 300 for the left ventricle delivery approach is positioned in the left ventricle LV from the aorta A, with access through the femoral artery. Delivery catheter 300 includes a main catheter 301 and two curved catheters 302, 303 extending from main catheter 301 and configured to curve in substantially opposite directions to one another. Main catheter 301 defines two side-by-side lumens (not shown) extending along the length of the catheter. Each curved catheter 302, 303 is disposed inside a respective lumen of catheter 300 and is capable of moving relative to main catheter 300 within the lumen. Curved catheters 302, 303 each have two anchoring balloons disposed near their distal ends and lumens in fluid communication with each balloon to facilitate inflation, in a manner similar to that described with respect to the right ventricle delivery catheter shown in FIG. 16. Curved catheters 302, 303 are independently manipulable, both in axial translation and in rotation relative to the main catheter. Moreover, it is contemplated that curved catheters 302, 303 can have the form of the adjustably curvable catheters discussed with reference to FIGS. 1 and 23. That is, it is contemplated that a pull-wire could be used to independently and adjustably curve the end portions of each catheter, thereby allowing for more control over the curve of the tip portion of each catheter.

Figure 18:
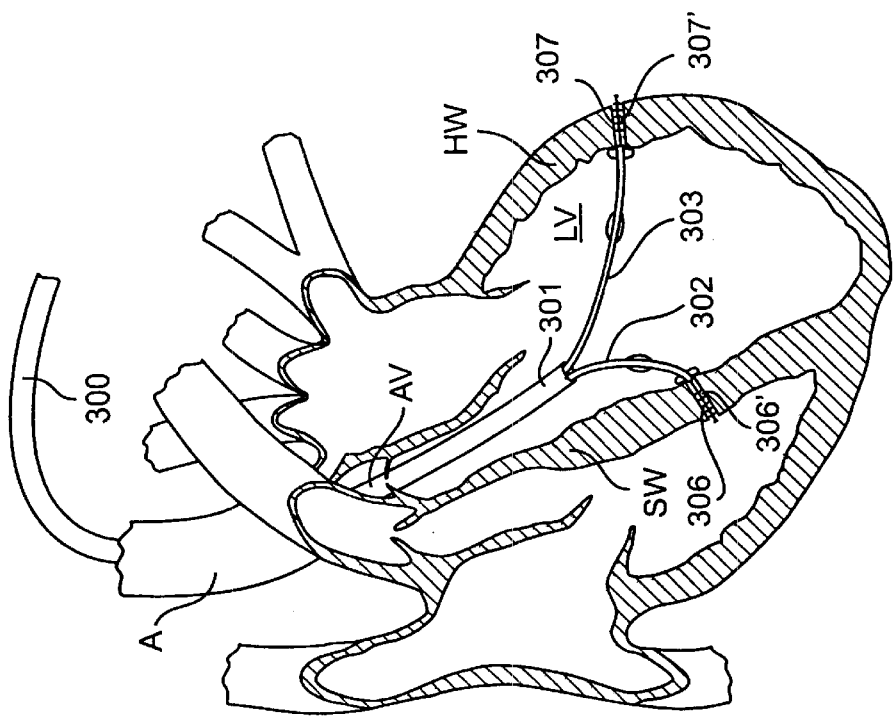
FIG. 18 is a vertical cross-sectional view of a heart showing the curved delivery catheters of FIG. 17 with inflated distal balloons respectively in contact with the free wall and septal wall of the heart and with sharpened wires respectively extending through the free wall and septal wall of the heart according to an aspect of the present invention.

Once the distal tip of main catheter 301 resides in the left ventricle LV, curved catheters 302, 303 are advanced with their respective distal anchoring balloons 304, 305 inflated. Distal balloons 304, 305 serve to act as protective bumpers on the curved catheters so as to avoid damaging various heart structures as the catheters traverse the ventricle. The curvature of catheters 302, 303 causes the tips of the catheters to deflect laterally until the distal balloons 304, 305 of each catheter 302, 303 contact the inside surface of the left ventricle LV, at the septal wall SW and free wall HW respectively. Once positioned, the curved catheters press against each other to form a self-supporting structure which remains in place during the beating of the heart. Once distal balloons 304, 305 contact the walls, sharpened wires 306, 307, similar to the one described above in the right ventricle delivery method and shown in detail in FIG. 15, are advanced into the myocardium, as shown in FIG. 18. As with the right ventricle delivery method, catheters 302, 303 are manipulated under ultrasonic and/or fluoroscopic guidance until the tips of the curved catheters are in a desired position on the free wall and septal wall for splint attachment. This permits a good bisection of the left ventricle LV and the avoidance of significant coronary structure. As discussed above, a "pigtail" catheter may also be used to help visualization and positioning of the devices, preferably with a diagnostic catheter in the coronary ostia. As with the wire used for the right ventricle approach, sharpened wires 306, 307 also have soft, preferably polymeric, threads 306', 307' disposed on their surfaces around their distal ends, to allow for screwing into the myocardium.

Curved catheters 302, 303 then are advanced with both anchor balloons deflated over wires 306, 307, similar to the step described above in the right ventricle approach. After catheters 302, 303 have been advanced across the ventricular walls SW, HW at the appropriate positions, both balloons on each of curved catheters 302, 303 are inflated to keep the catheters securely positioned and stabilized with respect to the chamber walls, as shown in FIG. 19.

Figure 20:
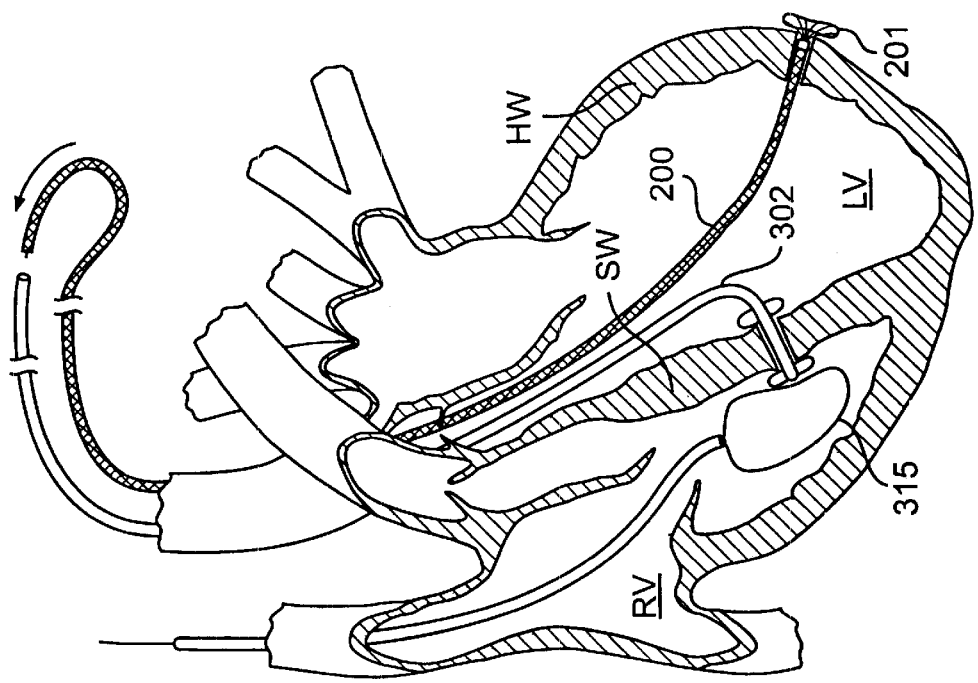
FIG. 20 is a vertical cross-sectional view of a heart showing the curved catheter contacting the free wall of FIG. 18 removed from the patient and the tension member being fed into a proximal end of the curved catheter contacting the septal wall of FIG. 18 according to an aspect of the present invention.
Figure 19:
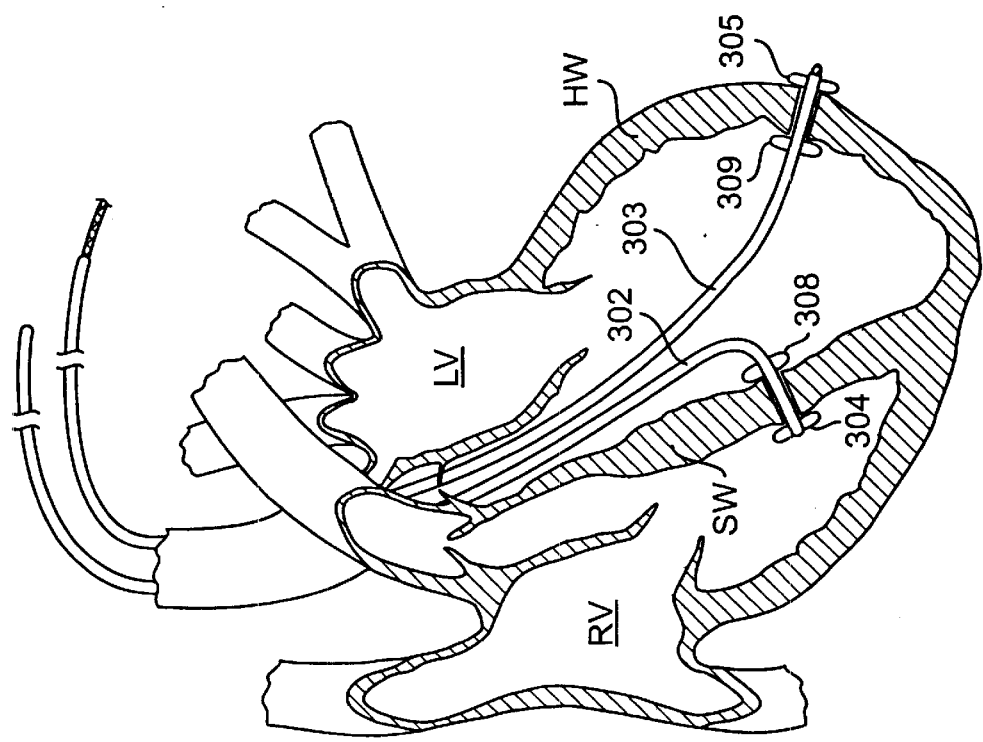
FIG. 19 is a vertical cross-sectional view of a heart showing a tension member delivered through the curved delivery catheter contacting the free wall of FIG. 18 according to an aspect of the present invention.

A tension member 200, with a first heart-engaging assembly, preferably in the form of a deployable fixed anchor pad mechanism 201 (free wall anchor), on its distal end, similar to the tension member and deployable fixed pad mechanism discussed with respect to the right ventricle delivery method, is inserted into curved catheter 303 engaging the free wall HW, as shown in FIGS. 19 and 20. Fixed pad 201 deploys in a manner similar to that of the right ventricle delivery approach. After fixed pad 201 is deployed, curved catheter 303 is removed, as shown in FIG. 20. The free end of tension member 200 opposite to the end on which fixed pad 201 is secured is inserted into the proximal end of curved catheter 302 that is engaged with septal wall SW. Tension member 200 is then advanced through the lumen of catheter 302 until it extends out of the distal end of the catheter and into right ventricle RV. A conventional snare 315, for example with a wire loop on its distal end, may be positioned in the right ventricle through an access site, preferably in a jugular vein, for example. As the free end of tension member 200 emerges from curved catheter 302 and into right ventricle RV, snare 315 captures tension member 200 and pulls tension member 200 out of right ventricle RV and out of the patient's body.

Figure 22:
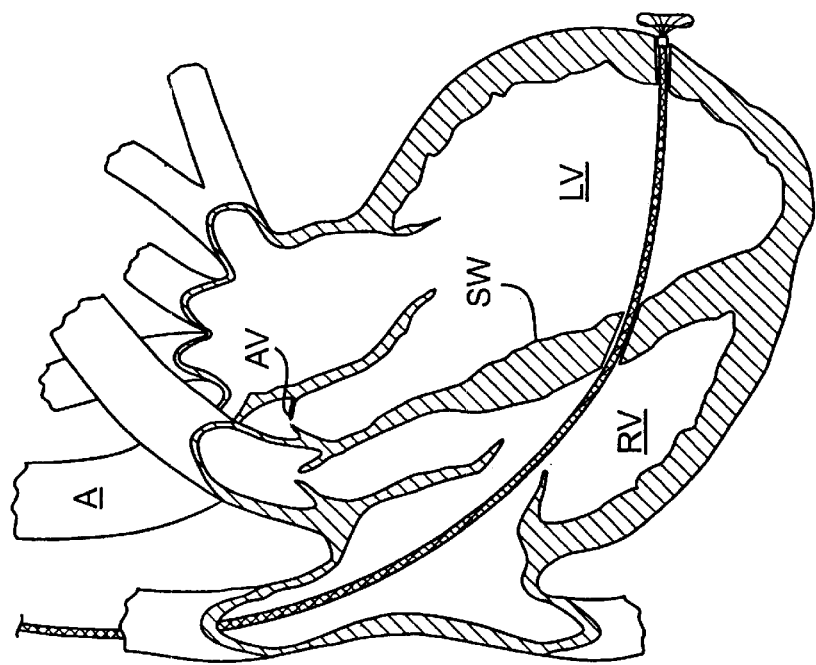
FIG. 22 is a vertical cross-sectional view of the heart showing the tension member of FIG. 21 extended across the left ventricle after the curved delivery catheter of FIG. 21 has been removed according to an aspect of the present invention.
Figure 21:
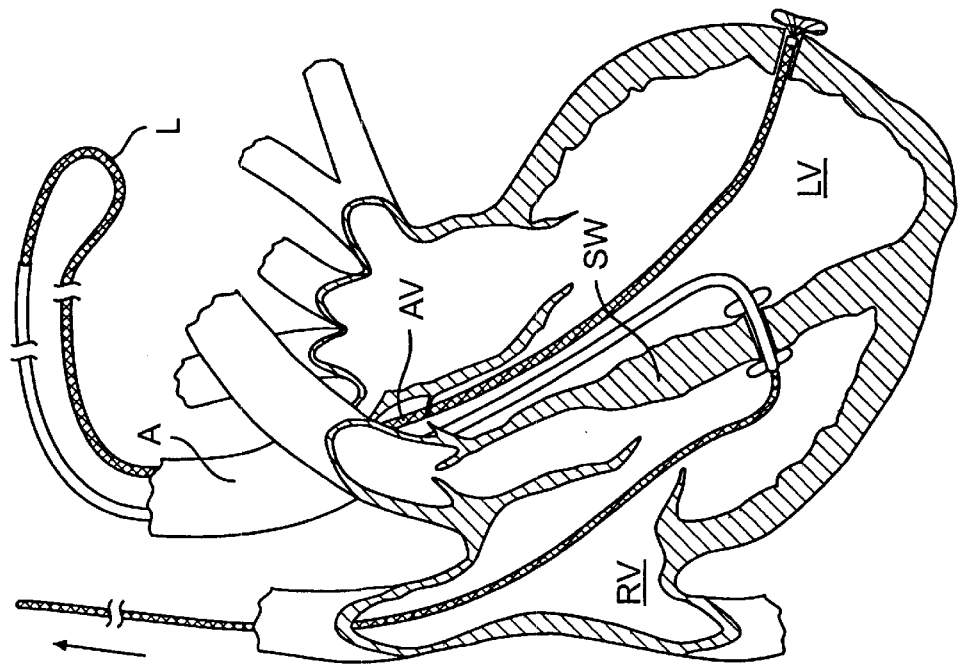
FIG. 21 is a vertical cross-sectional view of the heart showing the tension member of FIG. 20 being advanced through the curved catheter, through the septal wall, into the right ventricle and out of the heart according to an aspect of the present invention.

FIG. 21 shows tension member 200 after the free end has been snared and pulled out of the jugular vein access site. Tension member 200 preferably is long enough to allow for the withdrawal of catheter 303 that engages the free wall HW, the re-advancement of tension member 200 into catheter 302 that engages the septal wall SW, and the withdrawal of tension member 200 out of the right ventricle RV and the access site. Additionally, the proximal loop extending out the femoral access site (shown in FIG. 20) must still have enough length for the second catheter to be withdrawn. As second catheter 302 is withdrawn out of the femoral access site and over tension member 200 secured to the free heart wall, it preferably is removed from tithe tension member by skiving the length of the catheter down the lumen containing the tension member. FIG. 22 shows tension member 200 after curved catheter 302 has been fully removed.

At this point, tension member 200 is in a configuration similar to that shown in FIG. 7, and the technique described with reference to the right ventricle approach above to deliver and secure a second heart-engaging assembly, preferably in the form of an adjustable anchor pad (septal wall anchor), onto tension member 200 adjacent the septal wall SW to finish the splint deployment across the left ventricle LV can be used. Thus, the left ventricle delivery method and right ventricle delivery method differ only up to the point of delivery of the adjustable pad, and after that the steps may be the same.

FIGS. 23–30 illustrate yet another embodiment of a method for delivering and implanting a splint across the left ventricle from a free wall HW to a septal wall SW. The method shown in these figures is similar in many respects to the right ventricle delivery technique described above. However, the method to be described differs from the previously discussed right ventricle approach in that the splint is advanced across the left ventricle LV over a small hollow guidewire or needle of the type shown in FIGS. 24–27. Additionally, an alternative free wall deployable anchor structure is described.

In FIG. 23, a guide device, again preferably in the form of a delivery catheter 400, is positioned in the right ventricle RV from an access point, such as, preferably the right jugular vein, for example. Delivery catheter 400 has a similar structure as delivery catheter 100 used in the right ventricle delivery technique described above. However, delivery catheter 400 does not advance into and across the left ventricle LV, as did delivery catheter 100. Catheter 400 has a curved distal tip portion 400'. A tether, or pull-wire, 405 connected to distal tip portion 400' is configured to adjust the angle or curvature of the tip portion 400'. Tether 405 runs inside a lumen 420 disposed adjacent catheter 400, or, alternatively, within catheter 400. Pulling proximally on tether 405 causes tip portion 400' to deflect laterally. Delivery catheter 400 also includes a pre-formed support wire 410 configured to extend via advancement of the support wire from another lumen 421 disposed adjacent catheter 400 on a side substantially opposite to the side lumen 420 is. Support wire 410 not only assists to maintain the placement of tip portion 400' of delivery catheter 400 within right ventricle RV in the appropriate position, but also assists in positioning the tip portion 400' near the center of right ventricle RV relative to the anterior and posterior ends of the right ventricle, as a result of the shape and size of the support wire. Alternative shapes of the pre-formed support wire also are contemplated which would facilitate tip positioning and support in other desired positions within right ventricle RV.

Figure 24:
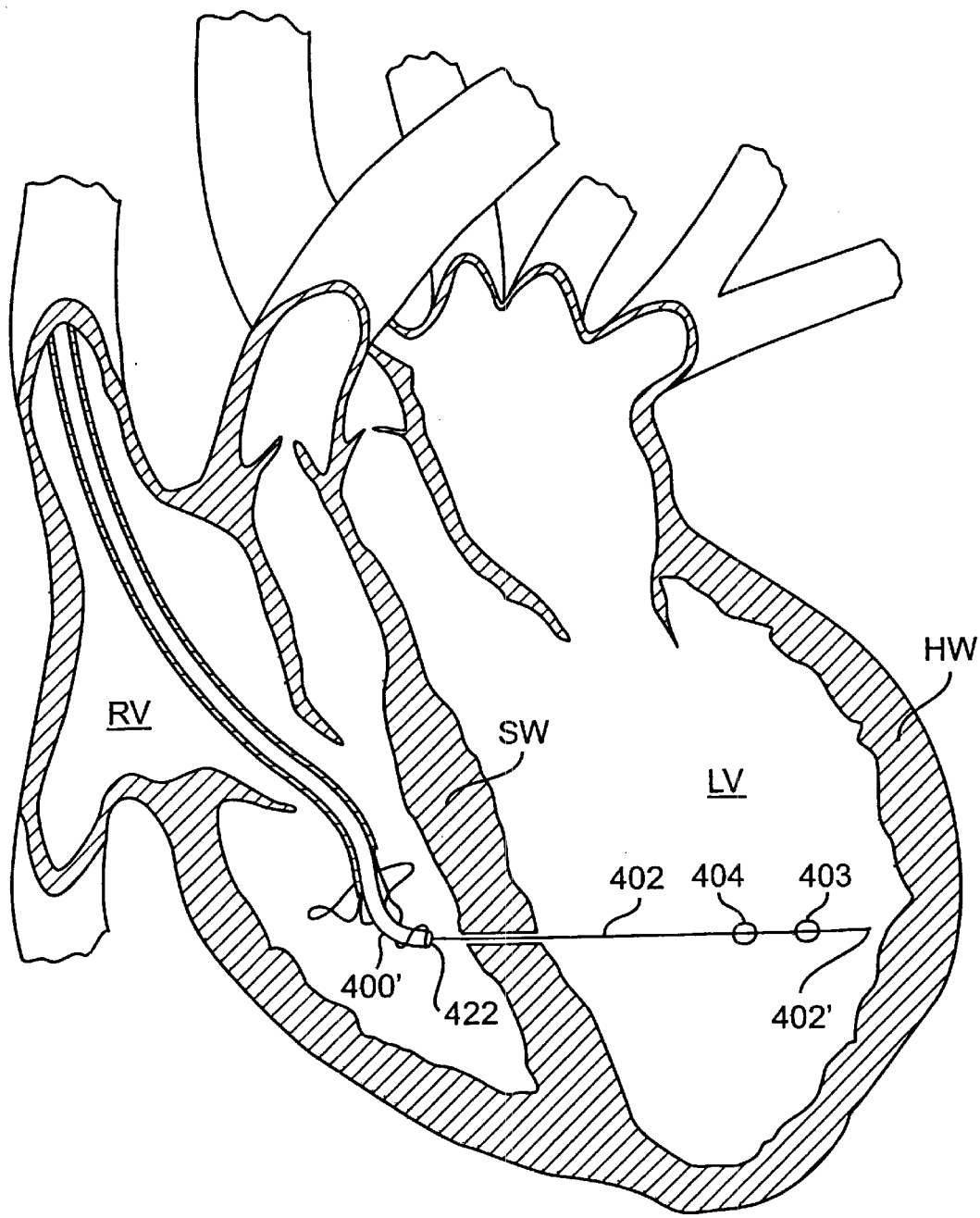
FIG. 24 is a vertical cross-sectional view of the heart with a guidewire with inflated balloons on a distal end extending from the delivery catheter of FIG. 23, through the septal wall, and across the left ventricle according to an aspect of the present invention.

After tip portion 400' of delivery catheter 300 is positioned and oriented in the desired location with respect to septal wall SW, a hollow sharpened metallic guidewire, or needle, 402 is advanced through a central lumen 422 of delivery catheter 400, across the ventricular septum SW, and across the left ventricular chamber LV to free wall HW, as shown in FIG. 24. As with the methods described above, a combination of fluoroscopic and ultrasonic imaging are performed to assist in the guidance and confirmation of positioning for this delivery technique. Appropriate radiographic or other suitable visible markers are positioned on the devices to facilitate this imaging, as described above.

Hollow guidewire 402 has a sharpened tip 402' and defines a central lumen plugged near tip 402'. The material used to make guidewire 402 preferably includes a super-elastic nickel titanium alloy, or other similar like material. Two elastomeric balloons, a distal balloon 403 and a proximal balloon 404, are secured near the distal end of guidewire 402 slightly proximal to sharpened tip 402'. Distal balloon 403 is in flow communication with central lumen 422 of guidewire 402. Proximal balloon 404 is in fluid communication with an additional tube (not shown) positioned inside hollow guidewire 402. In this manner, each balloon 403, 404 can be independently inflated and deflated as required.

Balloons 403, 404 preferably are in a deflated condition as they are advanced across septal wall SW and then are inflated during advancement across the left ventricle LV. Inflating the balloons during advancement across the left ventricle LV may assist in visualizing the advancement path of the guidewire. To assist in such visualization, preferably the balloons are inflated with a radiographic contrast agent. The ability to visualize the advancement path of guidewire 402 may prevent damage to various cardiac structure as well as assist in ensuring proper positioning of the guidewire on the free wall HW.

Figure 25:
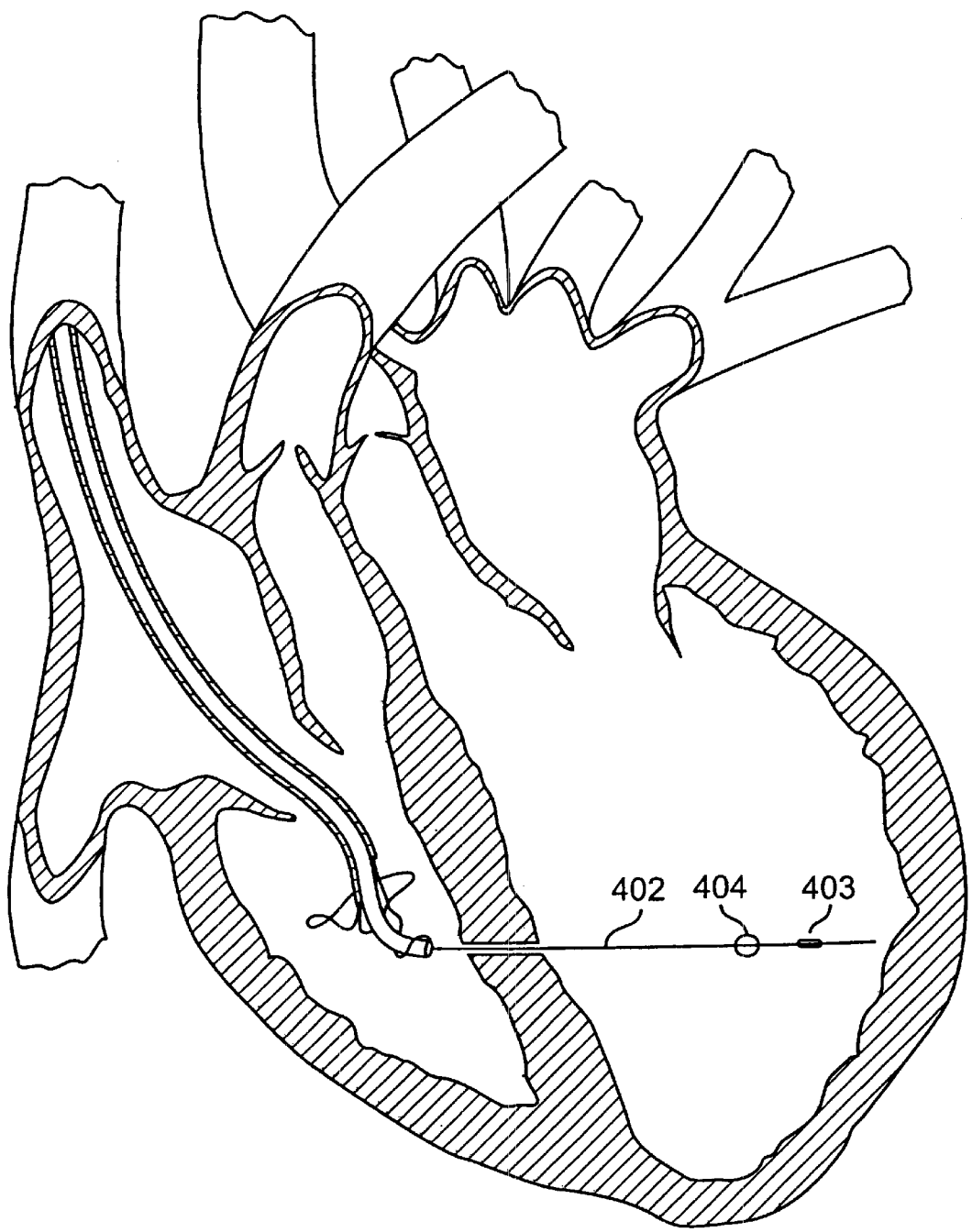
FIG. 25 is a vertical cross-sectional view of the heart showing the guidewire of FIG. 24 with the distal balloon deflated and about to be advanced through the free wall of the left ventricle according to an aspect of the present invention.
Figure 26:
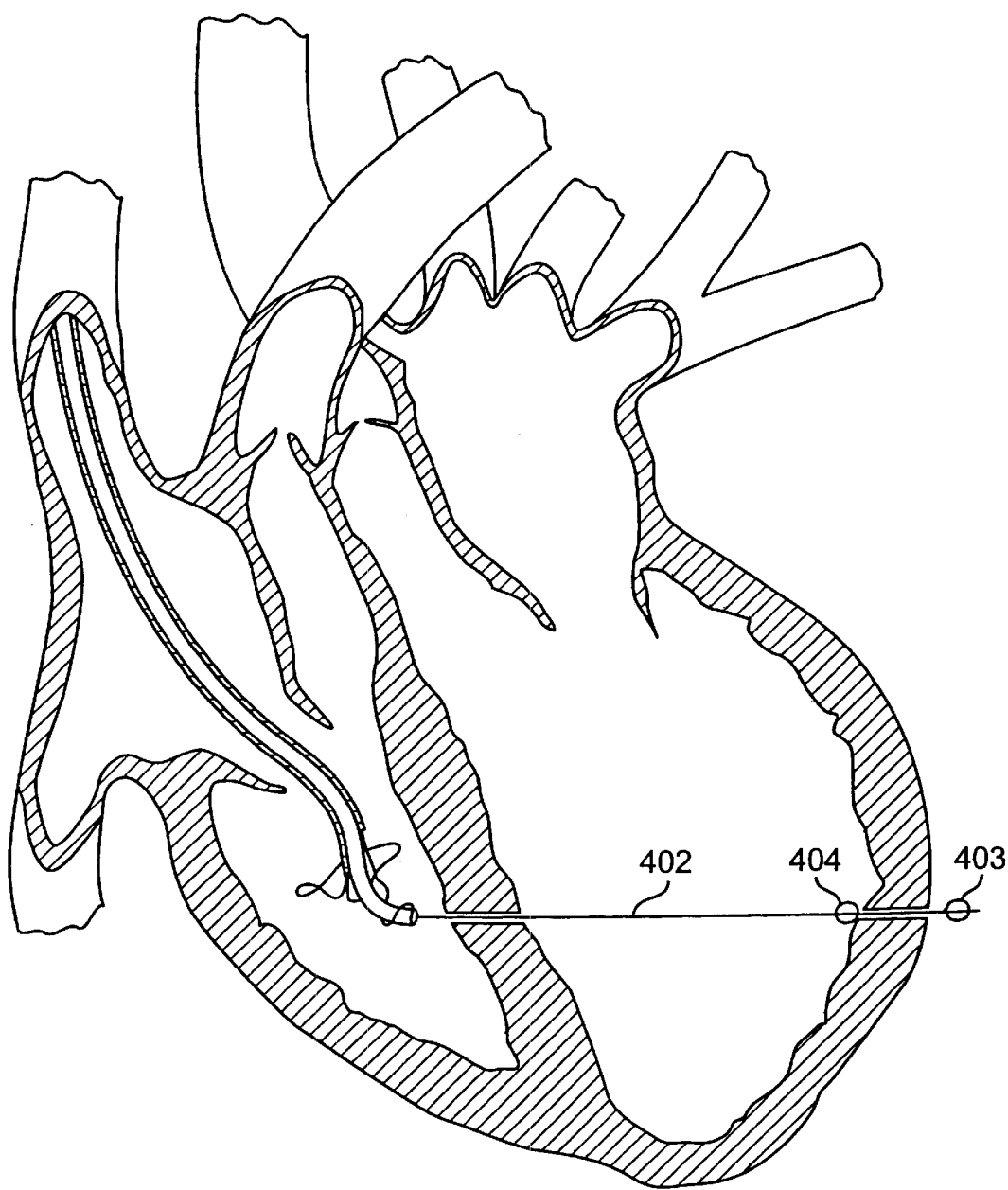
FIG. 26 is a vertical cross-sectional view of the heart showing the guidewire of FIG. 25 advanced through the free wall until the proximal inflated balloon abuts the inside of the free wall and with the distal balloon inflated according to an aspect of the invention.

As guidewire tip 402' approaches free wall HW, distal balloon 403 is deflated, as shown in FIG. 25, and the wire is further advanced into the free wall. Proximnal balloon 404 acts as a stop to limit advancement of guidewire 402 through free wall HW. This may eliminate or minimize any damage to tissue outside free wall HW of left ventricle LV. Once fully advanced, distal balloon 403 is re-inflated to secure the position of guidewire 402 across the left ventricular chamber, as shown in FIG. 26. It is preferred that the distance between balloons 403, 404 approximates the thickness of the heart wall.

Figure 27:
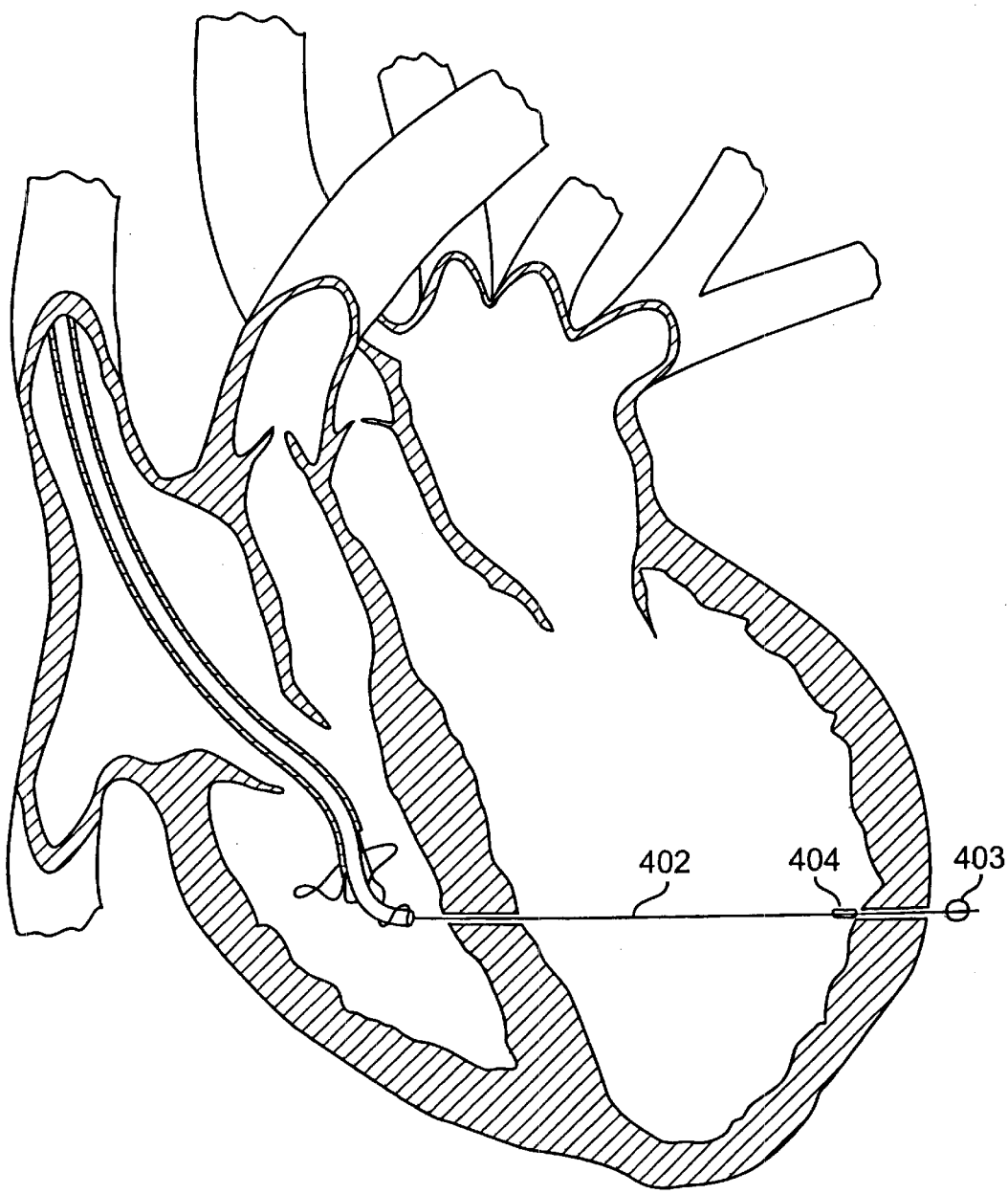
FIG. 27 is a vertical cross-sectional view of the heart showing the guidewire in the position of FIG. 26 with the proximal balloon deflated according to an aspect of the present invention.
Figure 28:
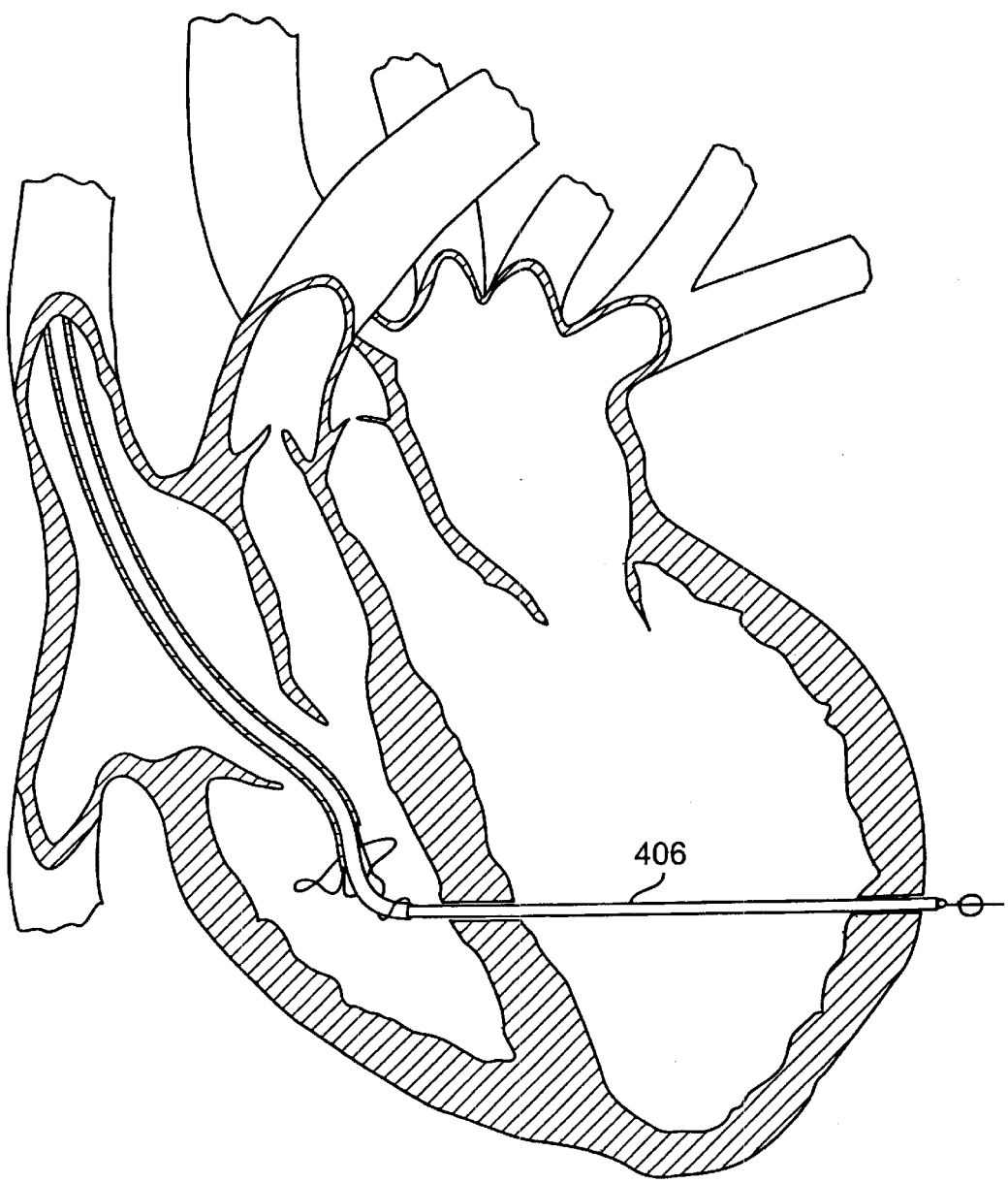
FIG. 28 is a vertical cross-sectional view of the heart showing a splint advancement catheter placed over the guidewire of FIG. 27 according to an aspect of the present invention.
Figure 31:
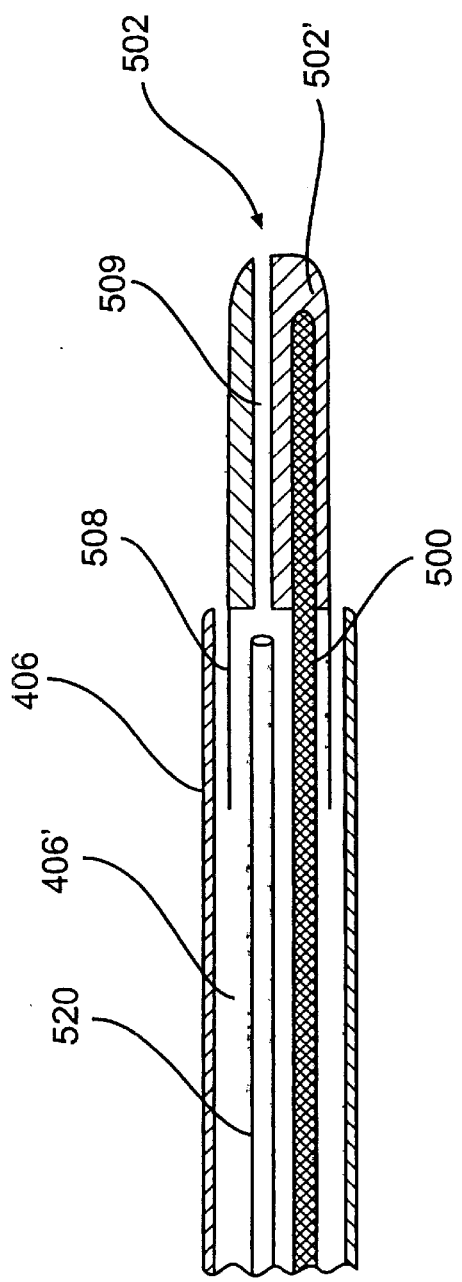
FIG. 31 is a partial, detailed cross-sectional view of the splint advancement catheter, tension member and distal anchor of FIG. 28 according to an aspect of the present invention.

Proximal balloon 404 is then deflated, as shown in FIG. 27, and a splint advancement catheter 406 carrying the tension member 500 and fixed deployable anchor 502 is advanced over guidewire 402, as shown in FIG. 28. The structure of splint advancement catheter 406 with respect to the delivery of the tension member 500 and deployable anchor 502 will now be described in more detail with reference to FIG. 31. As shown, catheter 406 defines a lumen 406' through which braided tension, member 500 is configured to extend. Tension member 500 is secured within a distal adhesive portion 502' of a deployable anchor 502. This adhesive portion preferably is made of a high strength adhesive such as epoxy, or the like and is also configured to slide through lumen 406'. A lumen 509 extends through fixed deployable anchor 502 adjacent to tension member braid 500. This lumen also is formed simultaneously within adhesive portion 502' of anchor 502. Lumen 509 and lumen 406' both pass over the outside of guidewire 402 (not shown) as advancement catheter 406 carrying tension member 500 with deployable fixed anchor 502 on one end is advanced across the left ventricle LV and through the free wall HW. Anchor 502 preferably is in the form of an elastic or super-elastic metallic tube including a plurality of preformed tabs 508 extending proximally from adhesive tube portion 502'. The tabs 508 may be formed by several longitudinally-oriented cuts along a portion of the length of the tube. During advancement of tension member 500, tabs 508 are prevented from flaring outward by the sheath defining lumen 406' of splint advancement catheter 406, as shown in FIG. 31. Upon retraction of the sheath of splint advancement catheter 406, tabs 508 are able to expand radially outwardly to their preformed shape, thus defining distal anchor 502. A separate push tube 520 for pushing on anchor 502 as the catheter 406 is retracted from the tension member and fixed anchor assembly also is shown in FIG. 31. Push tube 520 is configured to pass over the outside of guidewire 402 within lumen 406' adjacent tension member 500 to engage with the adhesive portion 502' of anchor 502.

Aside from the configurations described above with reference to FIG. 31, the deployable fixed anchor may have a structure similar to that described above with reference to the right ventricle and left ventricle delivery techniques. Similarly, the deployable anchor configurations described in connection with FIGS. 29–31 may be used in conjunction with other delivery techniques described above. Also, the deployable anchor structures described in connection with the previous splint embodiments can be utilized in conjunction with this embodiment.

Elongate tension member 500 preferably is similar to that described above in connection with the right ventricle delivery method and comprises a braid of high strength polymer fibers, preferably Spectra or other suitable like ultra-high molecular weight polyethylene. Tension member 500 may also include a covering along its full length made of a thin expanded polytetrafluoroethylene. Alternatively, only, the region of tension member 500 which is disposed inside the ventricular chamber could include a covering.

Tension member 500 is thus advanced into position by sliding splint advancement catheter 406 carrying tension member 500 and anchor 502 over guidewire 402. That is, guidewire 402 will be placed within lumen 509 of anchor 502 and then within lumen 406' of the catheter 406. The lumen 406' and the lumen 509 will move relative to guidewire 402 to advance catheter 406, tension member 500, and anchor 502 in the configuration shown in FIG. 31 until deployable anchor 502 protrudes beyond the myocardium of free wall HW. Once tension member 500 and anchor 502 are positioned appropriately with respect to the left ventricle and free wall HW, that is, when anchor 502 retained within the catheter 406 protrudes beyond the freewall HW as shown in FIG. 28, catheter 406 is retracted off tabs 508. This retraction of catheter 406 enables tabs 508 to expand radially outward from the remainder of deployable anchor 502. Push tube 520 is used to maintain the position of the tension member 500 during the catheter's retraction to overcome any friction between catheter 406 and tabs 508. After anchor 502 is deployed, both catheter 406 and push tube 520 are removed from guidewire 402 and then guidewire 402 also is removed.

At this point in the splint delivery technique of FIGS. 23–30, that is, after the deployable fixed distal anchor has been positioned on free wall HW, similar steps as described in connection with both the right ventricle and left ventricle methods above may be followed for the deployment of a second, adjustable anchor pad and for tightening and securing of tension member with respect to the left ventricle. An alternative embodiment of an adjustable anchor to tighten and secure the tension member also may be used in connection with this splint delivery technique, as well as with the other techniques described above. In this alternative embodiment, the proximal anchor may have a similar structure as the distal fixed deployable anchor or may be separately slidable and adjustable on the tension member (such as the adjustable anchor shown in FIGS. 7–10). The proximal anchor also may be pre-attached at an appropriate position on the tension member to provide the desired amount of ventricular shape change.

Figure 38:
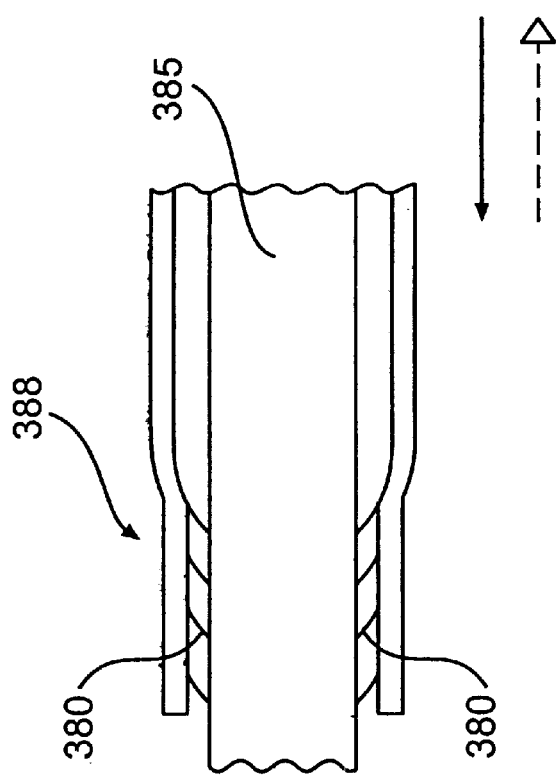
FIG. 38 is a cross-sectional view of an anchor assembly with an inner surface permitting movement with respect to a tension member in only one direction according to an aspect of the present invention.

In the case where the proximal anchor is slidable on the tension member, a one way "ratchet" or friction surface may be disposed on the inner surface of the tubular portion of the anchor to prevent its displacement in one direction. For example, as shown in FIG. 38, the inner surface of the tubular portion of the anchor can be in the form of rings or flared protrusions 380 that are angled with respect to the longitudinal axis of a tension member 385 as it is inserted into an anchor 388. The angled rings or protrusions 380 are configured so as to permit movement of the anchor with respect to the tension member in one direction but prevent movement in the opposite direction. As illustrated in FIG. 38, the rings or protrusions would permit movement in the direction of the solid arrow, but prevent movement in the direction of the dotted arrow by essentially digging into the tension member surface.

Figure 8:
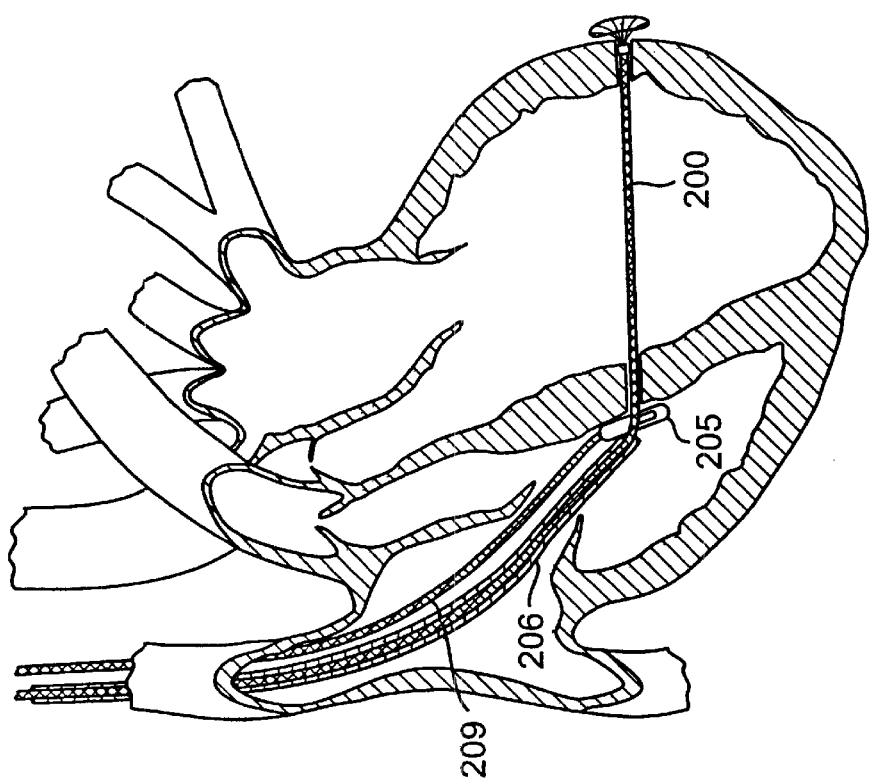
FIG. 8 is a vertical cross-section of the heart showing the securing of the adjustable anchor of FIG. 7 to the tension member to change the shape of the left ventricle according to an aspect of the present invention.
Figure 30:
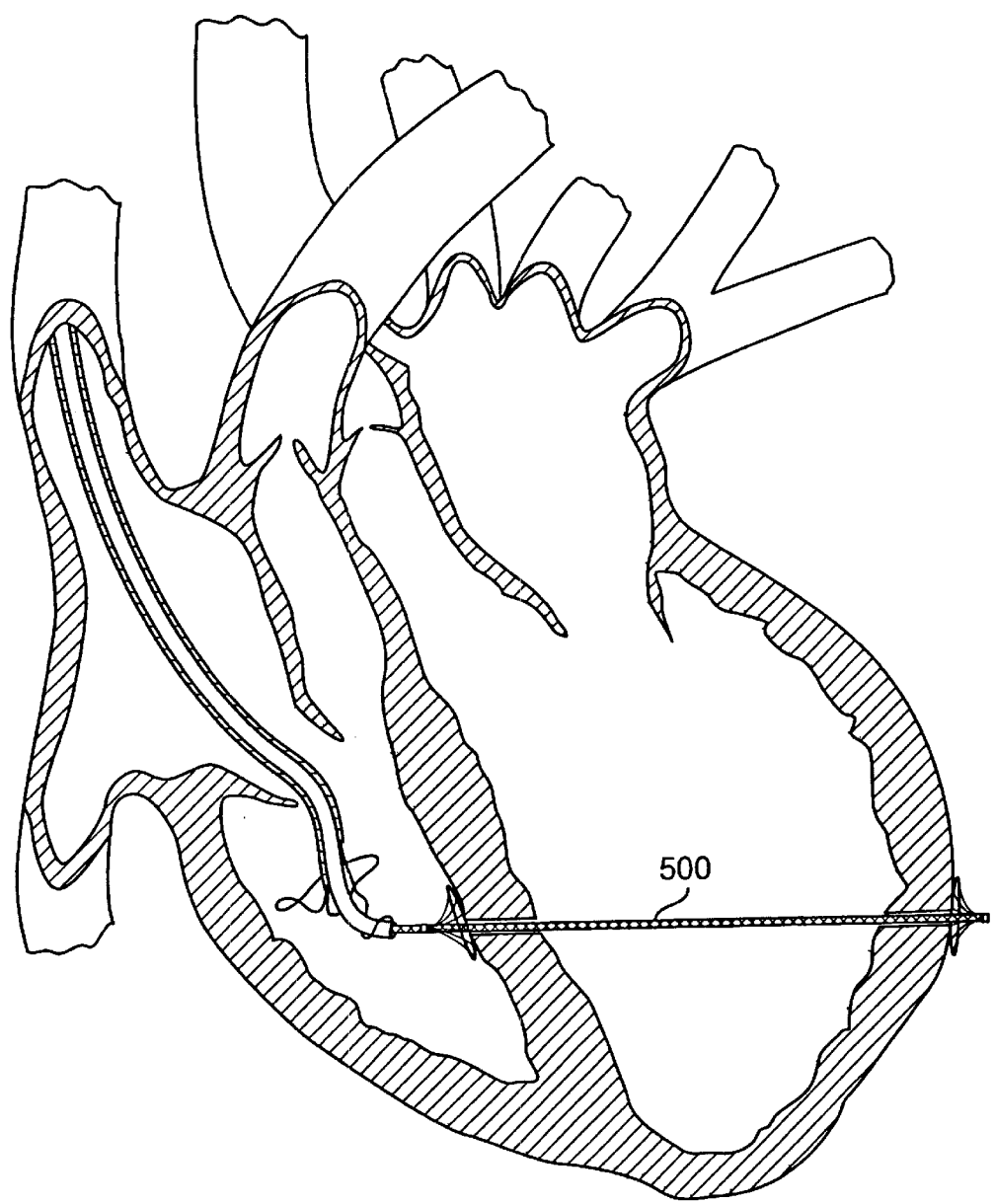
FIG. 30 is a vertical cross-sectional view of the heart showing the splint advancement catheter of FIG. 28 entirely removed and the splint assembly deployed across the left ventricle according to an aspect of the present invention.

A tightening device such as that described and shown in FIG. 8 may be utilized to advance the deployed anchor into position. In this case, the anchor may be initially positioned such that when the sheath of the splint advancement catheter is further withdrawn, the proximal anchor also would deploy within the right ventricle RV adjacent to the septal wall SW. The tightening device could then be used to advance the position of the proximal anchor to a desired position against the septal wall SW, as shown in FIG. 30. Alternatively, the delivery catheter itself could be used to advance the deployed proximal anchor to the desired position. Once the proximal anchor is to positioned to its appropriate location, any excess tension member length extending beyond the proximal anchor may be severed in a manner similar to that described above in connection with FIG. 9.

In the alternative case where proximal anchor is pre-attached at a specified distance from the distal anchor, the left ventricle should be deformed prior to the pad deployment. The delivery catheter can act as a temporary proximal anchor, while the tension member and distal anchor are pulled proximally. Once the proper shape change of the left ventricle is attained, the proximal anchor may be deployed, upon further retraction of the sheath of the splint advancement catheter. In this embodiment, preferably the distance between the distal and proximal anchors will be selected prior to delivery such that a desired shape change of the heart chamber may be obtained, since the adjustability of the shape change will be limited by the fixed position of the proximal anchor on the tension member. The delivery catheter may then be removed and excess tension member severed, again as described with reference to FIG. 9.

While the splint delivery methods and devices just described in connection with FIGS. 23–30 were in the context of a right ventricle approach, it is also contemplated to utilize the delivery devices and methods in a direct left ventricle approach as well. In a direct left ventricle approach, two delivery catheters simultaneously could be utilized to position a splint from within the left ventricle in manners similar to those described with reference to FIGS. 17–22.

Other embodiments of a deployable, fixed heart-engaging assembly, or anchor, also are contemplated as within the scope of the present invention and are shown in FIGS. 32–35. A preferred tension member used in the various embodiments of the present invention is described in the '049 application, incorporated by reference above, and is formed of several multifilament bundles of a high strength polymer. These bundles are braided together in a relatively tight configuration. Certain combinations of bundle size, number of bundles, and pick count, described in more detail in the '049 application, result in a braid with several preferred properties as also described in the '049 application, incorporated by reference above. One property that may result from such a braid construction includes a relatively stable braid diameter that does not deform to a great extent if subjected to axial compression or internal radially-outward directed forces. However, a braid formed with a lower pick count has a greater diametric expandability when subjected to such forces. For example, a braid woven of the same material and having approximately 16 to approximately 64 bundles and approximately 2 to approximately 15 picks per inch may more readily expand in diameter, upon the application of a radial force directed outwardly from within the braid. This expandable property of a braid can be utilized in the formation of yet another alternative deployable anchor structure.

Figure 32:
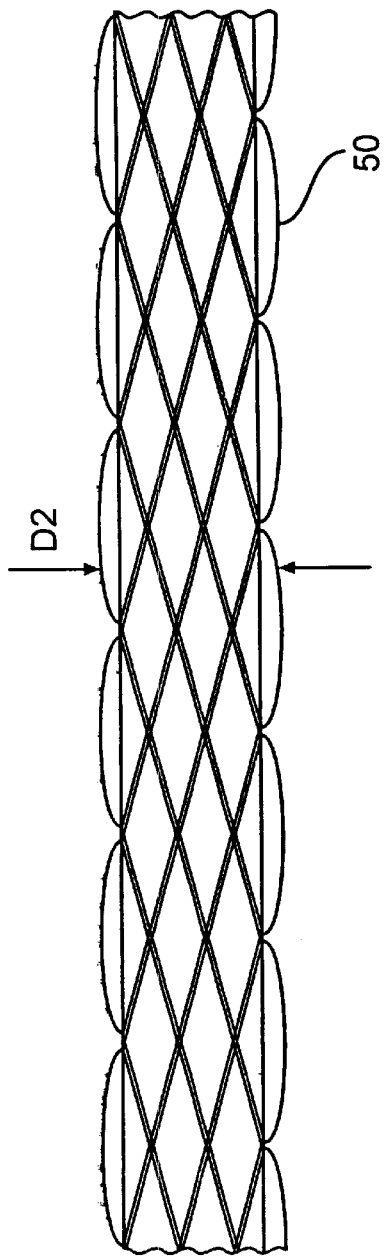
FIG. 32 is a partial side view of a braided tension member according to an aspect of the present invention.
Figure 33:
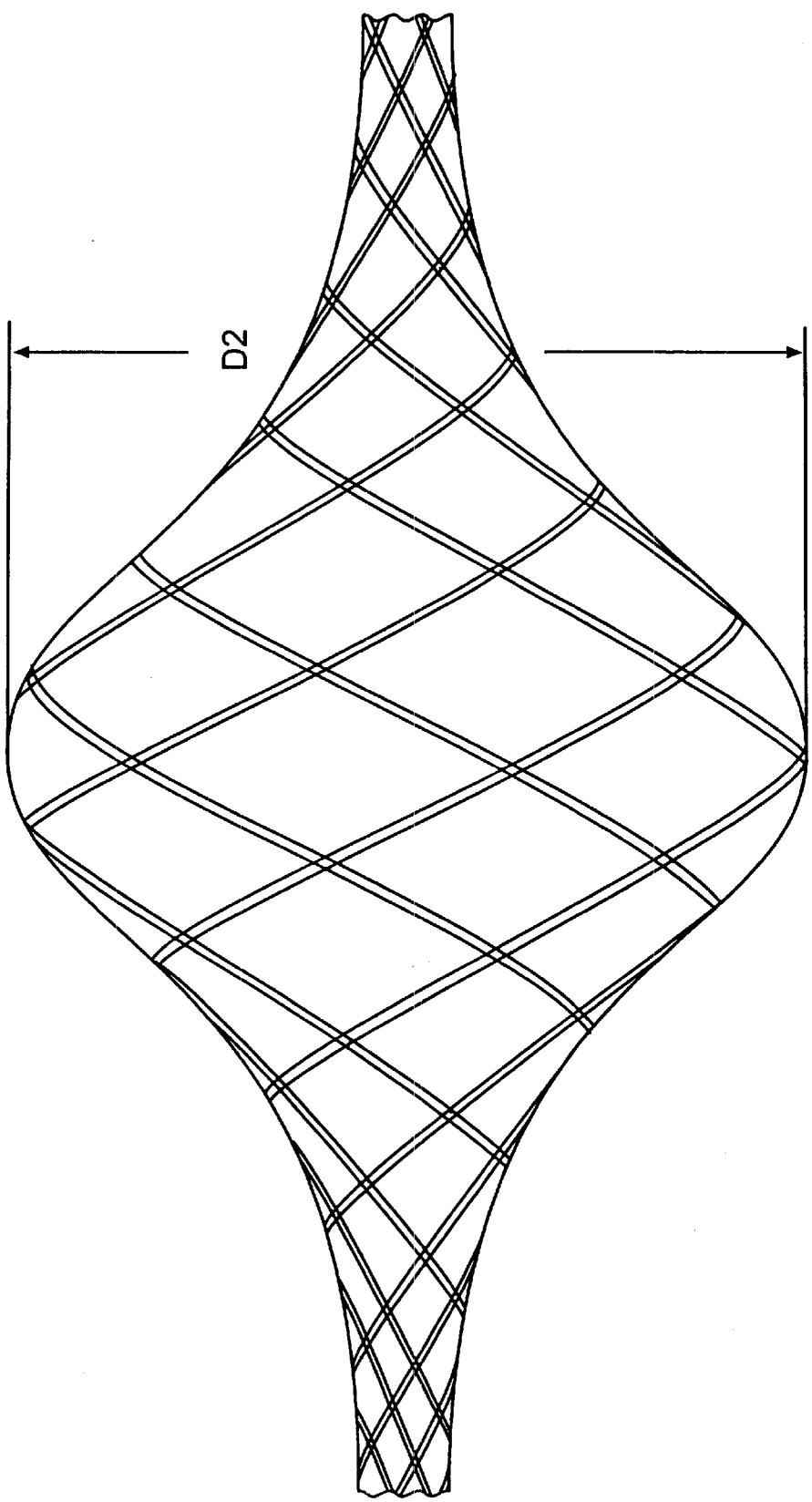
FIG. 33 is a partial side view of a braided tension member having a diametrically expandable portion according to an aspect of the present invention.

For example, FIG. 32 is a relatively simplified schematic illustrating a tension member 50 formed of a braid of relatively low pick count in its natural (i.e., non-stressed) as-braided condition. The braid is uniformly relatively small in outer diameter $D_1$. When the braid is under tension, and absent any other deforming forces, the diameter $D_1$ of the braid remains relatively small. FIG. 33 illustrates the same braided tension member 50 as in FIG. 32, but shows the braid with a local application of an outward radially directed force from within the braid. Since the braid pick count is relatively low, the braid has the capacity to expand at the point of application of the radial force to a diameter $D_2$, which is several times its original diameter $D_1$.

Figure 34:
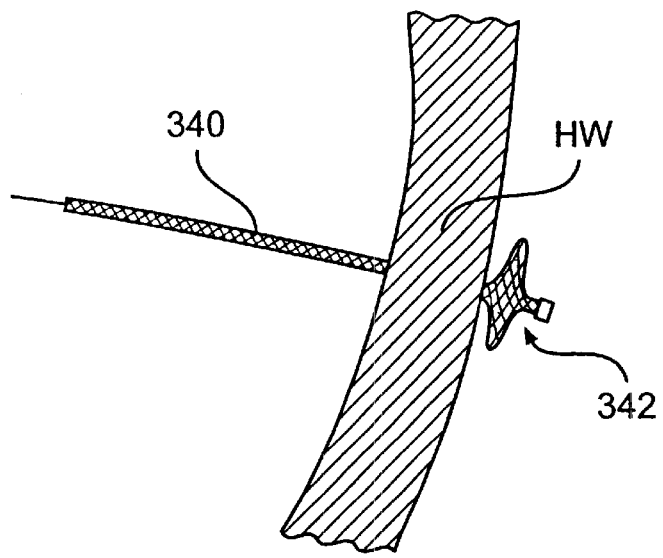
FIG. 34 is a partial perspective view of the tension member of FIG. 33; forming a free wall anchor at the diametrically expandable portion according to an aspect of the present invention.
Figure 34A:
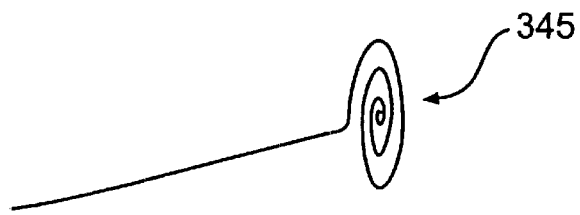
FIG. 34a is a partial perspective view of a spiral-shaped deployable wire used to diametrically expand the tension member of FIG. 33 to form the anchor of FIG. 34 according to an aspect of the present invention.
Figure 34B:
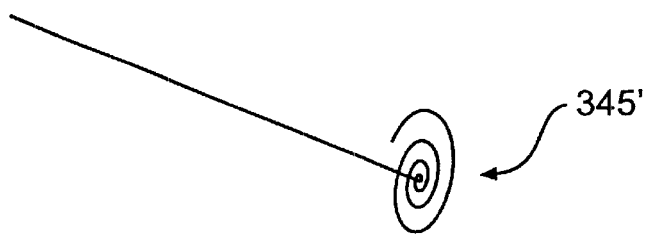
FIG. 34b is a partial perspective view of a spiral-shaped deployable wire used to diametrically expand the tension member to form the anchor having a spiral formed in an opposite direction to the spiral of FIG. 34a according to another aspect of the present invention.

FIG. 34 shows a tension member 340 having a braid configuration such as that shown in FIGS. 32 and 33 utilized for an integral expandable distal anchor 342 of tension member 340. At least a portion of the tension member 340 is woven at a relatively low pick count to allow for that portion to form into the expandable distal anchor 342. Alternatively, the entire tension member 340 can be uniformly woven at the relatively low pick count. Several methods for creating an outward radial force from within the braid to form anchor 342 are contemplated. These methods include using an elastic or shape memory wire disposed inside the braid of tension member 340 during placement across the ventricular wall HW. A preferred wire 345 is shown in FIG. 34a. Note that it is contemplated that the direction of spiral of the wire can be opposite to that shown in FIG. 34a, as shown in FIG. 34b. Wire 345 preferably has a natural shape in the form of a disc-shaped spiral. When tension member 340 is delivered using a splint advancement catheter of the types described above, the spiral will have a straightened configuration. Upon removal of the of the splint advancement catheter from the portion of the tension member 340 which will form the distal anchor 342, however, the spiral shape of wire 34 may be re-established, thereby forcing the braided portion surrounding it to expand in diameter into a disc-like shape, as shown in FIG. 34. The wire may either be pre-loaded into the tension member or may be advanced into the tension member once the tension member has been positioned with respect to the heart wall and the catheter has been retracted enough to expose a portion of the tension member that is outside the heart wall HW. The force of the catheter on the wire keeps the wire in its straightened configuration. The smaller diameter portion of the spiral forms first, and as more of the wire is advanced through the tension member beyond the catheter, the spiral grows in diameter until the full spiral is re-established. Alternatively, as shown in FIG. 34b, the large diameter portion of the spiral may form first, as the wire 345' is advanced. To help prevent wire 345 from penetrating through the interstices of the braid of tension member 340, a thin membrane, preferably made of an elastic material for example, is disposed along the inside of the braid in the area where the spiral portion of wire 345 is positioned.

In this embodiment, wire 345, particularly in the spiral region, preferably will remain together with the braid of tension member 340 even after diametric expansion in order provide the anchoring rigidity needed to secure the splint in place on the heart. Initially, the spiral portion of wire 345 may carry a significant portion of the load of anchor 342. However, it is anticipated that over time, the expanded braid forming anchor 342 would become ingrown with scar tissue, and therefore a relatively large portion of the chronic mechanical loading may be carried by the filaments of the braid. Using filaments of ultra-high molecular weight polyethylene has been shown to produce a tension member and anchor having high strength and high fatigue resistance. A portion of the wire that does not form the spiral may be removed, for example by torquing the wire and breaking it at a location slightly proximal to the spiral.

To prevent any of the braided portion distal of the expanded region from "creeping" back over the spiral region, the distal most region of the braid preferably is either fused or banded. This will prevent expansibility in those regions. Alternatively, those regions of the braided tension member could be woven with a higher pick count.

Figure 35:
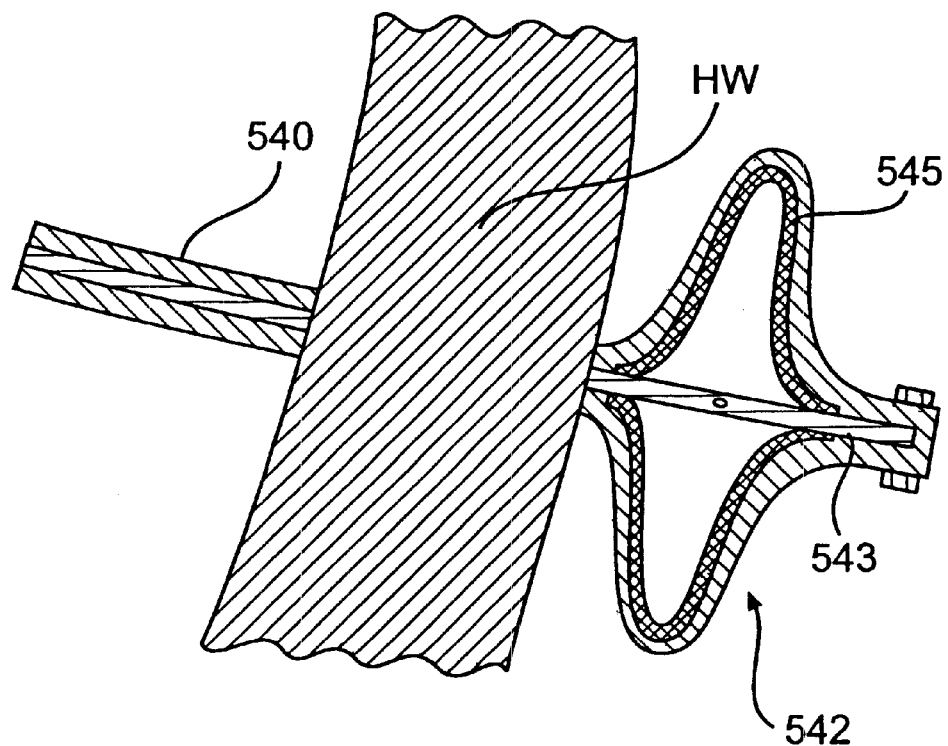
FIG. 35 is a partial perspective view of a diametrically expandable tension member forming an anchor portion by using an inflated balloon within the expandable portion of the tension member to cause diametric expansion according to an aspect of the present invention.

An alternative device for causing expansion of an expandable braid portion of a tension member 540 includes an inflatable balloon disposed inside braided tension member at the expandable portion forming the anchor, as shown in FIG. 35. Inflatable balloon 545 can be positioned in the desired location within tension member 540 either before advancement of the tension member across the ventricular wall, or after, as shown in FIG. 35. Preferably, balloon 545 is formed of an elastomeric material such as silicone or urethane, or the like, and has a disc-like shape upon expansion. A lumen 543 connecting the interior of balloon 545 to an inflation device (not shown) may extend along the inside of braided tension member 540. In a preferred embodiment, the material used to expand balloon 545, and thus the region of the braided tension member 540 forming distal, deployable anchor 542, includes a curable material such as RTV silicone, epoxy, urethane, or the like. Similar to the spiral anchor embodiment discussed above, the cured material forming the balloon may carry a significant load initially, but upon ingrowth of the expanded braided region of the tension member, the filaments of the braid would be the primary chronic load carrying members.

One of ordinary skill in the art would recognize that the alternative distal anchors described above could be utilized in conjunction with any of the delivery techniques of the present invention and could be used as either the free wall anchor or septal wall anchor with modifications as necessary.

Figure 29:
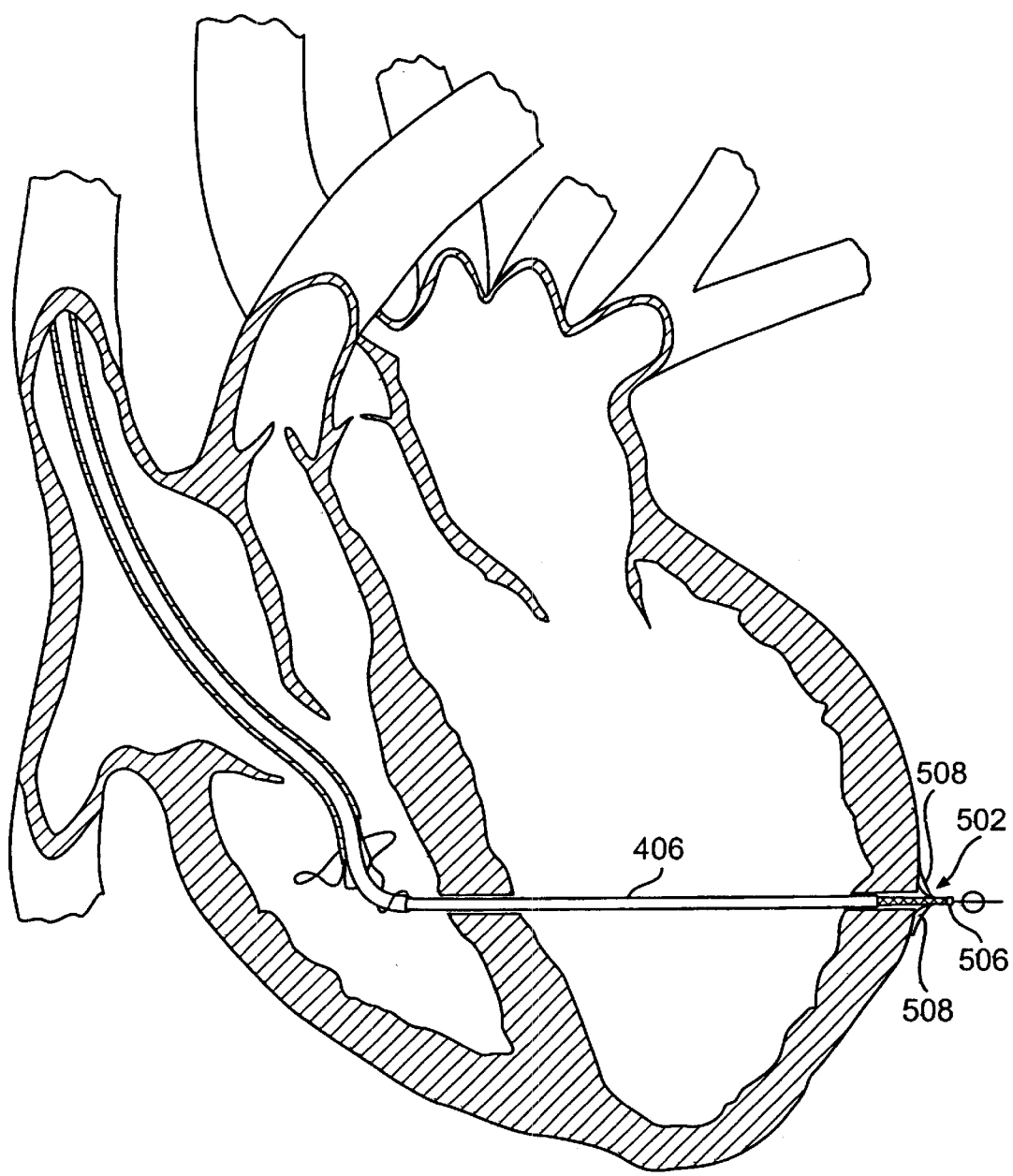
FIG. 29 is a vertical cross-sectional view of the heart showing the splint advancement catheter of FIG. 28 being removed from a tension member and deployable anchor of the splint according to the present invention.

Another alternative embodiment for an expandable anchor would utilize an anchor similar to the expandable tab anchor described above with reference to FIGS. 29–31. However, in this embodiment, that anchor would be merely temporary, and could be designed to be relatively small and low profile, for easy delivery, but may not have the adequate strength and durability to be a permanent chronic anchor. In this case, a permanent anchor, similar to the adjustable pad anchor assembly described in the '049 application incorporated above could be delivered as a replacement to that temporary anchor. Once the temporary anchor is positioned, as shown in FIG. 29, a small surgical incision may be made between the ribs adjacent the free wall HW of the left ventricle LV, thus creating an access port to deliver the permanent anchor. Alternatively, a trocar may be positioned in that same location. A snare device positioned within the it port or trocar can be used to grab the temporary anchor and tension member and pull the anchor off of the tension member and outside of the patient. An adjustable anchor pad as described in the '049 application and similar to the description of FIGS. 7 and 8 above then may be attached to the braid outside of the patient, using the staple methodology described previously with reference to FIG. 8 and the '049 application. The anchor can then be pulled back into position by retracting the other end of the tension member via the length of the tension member that remains outside the jugular vein. The septal wall anchor in this case preferably would be in the form of the solid anchor and delivered in the manner described above in conjunction with FIGS. 7–10. Overall, this procedure would be a combination endovascular and "minimally invasive" surgical operation. In this embodiment, preferably both anchor pads would be of a solid type construction.

An alternative proximal anchor also may utilize the expandable capability of a relatively low pick count braid, in a manner similar to that described above for the distal, or free wall, anchor. In this embodiment, the entire braid of the tension member preferably includes the relatively low pick count permitting diametric expansion. The tension member and distal anchor could be delivered using any of the approaches described herein, but preferably one of the right ventricle approach methods. After the distal, or free wall, anchor is delivered, the proper ventricle shape change can be induced using a tightening device in the form of a simple tube, such as the one described above, but without the anchor shown in FIG. 8. A balloon or spiral wire type of expander device as described in connection with the distal anchors shown in FIGS. 34, 34a, and 35, may be positioned in the proper location and caused to expand a portion of the braid external to the septal wall. If a balloon type expansion device is used, it may also include a detachable inflation tube, such that when the balloon is inflated with a curable material, the inflation tube can be removed prior to the excess tension member length being severed. It is also contemplated that such an expandable proximal anchor can be secured to the end of the tension member at a location adjacent to an exterior surface of a heart wall other than the septal wall, such as a wall surrounding the right ventricle, for example.

Figure 36:
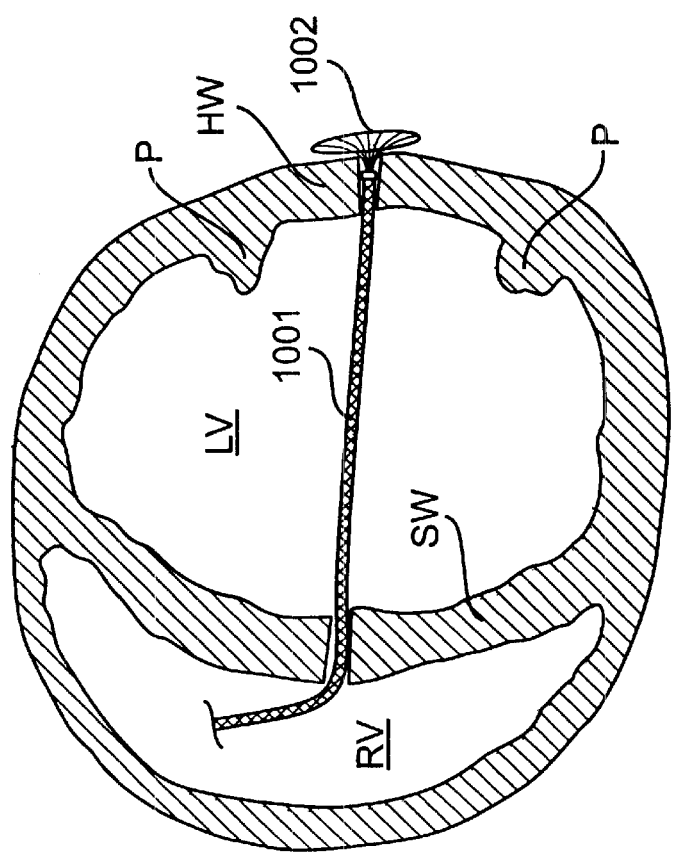
FIG. 36 is a transverse cross-sectional view of the heart showing a preferred placement of a tension member of a splint assembly to treat a mitral valve according to an aspect of the present invention.

The methods described above to place the splint assemblies with respect to the heart can be repeated for any desired number of splint assemblies to achieve a particular configuration. The length of the tension members extending between the free wall and septal wall anchors also can be optimally determined based upon the size and condition of the patient's heart. It should also be noted that although the left ventricle has been referred to here for illustrative purposes, the apparatus and methods of this invention can be used to splint multiple chambers of a patient's heart, including the right ventricle or either atrium, or can be used to aid the function of valves, such as the mitral valve. An example of a preferred position of a splint assembly 1000 improves mitral valve function, as well as reducing stress in the left ventricular walls. The valve function is improved by aiding in the apposition of valve leaflets when positioned as shown in FIG. 37. Preferably, three splints are placed in a coplanar fashion, bisecting the left ventricle LV of the heart. The superior-most splint 1000 is placed at approximately the level of the heads of the papillary muscles PM, and the additional two splints (not shown in FIG. 37) are placed inferiorly toward the apex. The preferred orientation shown in FIG. 37 both bisects the left ventricle LV and avoids key structures such as coronary vessels and the like. The splints according to this orientation also extend through the septum SW and enter a portion of the right ventricle RV. In the preferred placement, as with those described above, heart-engaging assemblies 1002, 1003 will be positioned adjacent an exterior surface of a free wall HW surrounding the left ventricle LV and adjacent an exterior surface of the septal wall SW within the right ventricle RV. Further details regarding splinting devices and methods for treating heart valves can be found in the application entitled "Methods and Devices for Improving Mitral Valve Function," to Richard F. Schroeder et al., filed on a date even herewith and incorporated by reference above. Although any of the delivery methods described above could be used to implant the splint device in this manner, FIG. 36 shows a short axis cross-section of a heart and a preferred endovascular technique wherein the elongate tension member 1001 having a deployable fixed anchor 1002 on its distal end is delivered through the right ventricle RV and then into the left ventricle LV.

Furthermore, the alignments of the splints with respect to the heart that are described above are illustrative only and may be shifted or rotated about a vertical axis generally disposed through the left ventricle and still avoid the major coronary vessels and papillary muscles. In addition, the inventive devices and methods can be implanted to treat a heart having aneurysms or infarcted regions similar to those described in prior U.S. application Ser. No. 09/422,328 discussed earlier herein and incorporated above.

The various components of the splint assembly to be implanted in the heart should be made of biocompatible material that can remain in the human body indefinitely. Any surface engaging portions of the heart should be a traumatic; in order to avoid tissue damage and preferably formed of a material promoting tissue ingrowth to stabilize the anchor pad with respect to the surfaces of the heart.

It will be understood that this disclosure, in many respects, is only illustrative. Changes may be made in details, particularly in matters of shape, size, material, number and arrangement of parts without exceeding the scope of the invention. Accordingly, the scope of the invention is as defined in the language of the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for placing a splint assembly transverse a heart chamber, the method comprising:
   providing an elongate member having a first end and a second end and a deployable heart-engaging assembly connected to said first end;
   advancing the elongate member through vasculature structure and into the heart chamber such that the first end of the elongate member extends through a first location of a heart chamber wall and the second end extends through a second location of a heart chamber wall substantially opposite the first location;
   deploying the deployable heart-engaging assembly such that it engages with a first exterior surface of a heart chamber wall adjacent the first location; and
   securing the elongate member with respect to the heart chamber with a second heart-engaging assembly connected to the second end, said second heart-engaging assembly engaging with a second exterior surface of a heart chamber wall adjacent the second location.

2. The method of claim 1, wherein the chamber is a left ventricle of the heart.

3. The method of claim 2, wherein the elongate member is advanced through a guide device endovascularly inserted into the right ventricle.

4. The method of claim 3, wherein the guide device is a catheter.

5. The method of claim 3, wherein inserting the guide device includes extending the guide device across the left ventricle from the right ventricle through the first location on a free wall surrounding the left ventricle and through the second location on a septal wall.

6. The method of claim 3, wherein inserting the guide device includes stabilizing the guide device with respect to the left ventricle.

7. The method of claim 6, wherein the stabilizing includes inflating balloons disposed proximate a distal end of the guide device.

8. The method of claim 7, wherein the stabilizing includes inflating a first balloon adjacent the first exterior surface of the heart chamber wall and a second balloon adjacent an interior surface of the heart chamber wall.

9. The method of claim 2, wherein the inserting includes inserting a guide device into the left ventricle without first entering another heart chamber.

10. The method of claim 9, wherein the guide device includes a first guide member and a second guide member, said first guide member being configured to extend toward a first interior surface of the chamber wall at the first location and said second guide member being configured to extend toward a second interior surface of the chamber wall at the second location.

11. The method of claim 10, wherein the inserting includes stabilizing said first guide member at the first interior surface and the second guide member at the second interior surface.

12. The method of claim 11, wherein the stabilizing includes inflating balloons disposed proximate the distal end of each of the first and second guide members.

13. The method of claim 12, wherein the stabilizing includes inflating a first balloon on each of the first and second guide members adjacent the first and second exterior surfaces of the chamber wall respectively and a second balloon on each of the guide members adjacent the first and second interior surfaces of the chamber wall.

14. The method of claim 10, wherein the first and second guide members are adjustably curvable catheters.

15. The method of claim 1, wherein the deploying the first heart-engaging assembly includes expanding at least a portion of the assembly.

16. The method of claim 15, wherein the expanding includes applying a outwardly directed force from within the portion of the assembly.

17. The method of claim 16, wherein the applying includes inflating the portion of the assembly.

18. The method of claim 1, wherein at least a portion of the first heart-engaging assembly is integrally formed with the elongate member.

19. The method of claim 1, wherein the securing with the second heart-engaging assembly includes adjusting a length of the elongate member between the first and second locations.

20. The method of claim 19, wherein the adjusting the length includes changing the cross-sectional shape of the heart chamber.

21. The method of claim 19, wherein the adjusting the length includes changing the radius of curvature of the heart chamber.

22. The method of claim 1, further comprising inserting a guide device through vasculature structure and into the heart, wherein the advancing includes advancing the elongate member through the guide device.

23. The method of claim 22, wherein inserting the guide device includes inserting the guide device through the chamber wall at the first and second locations.

24. The method of claim 23, wherein the inserting through the chamber wall includes advancing the guide device over a needle extending through the chamber wall at the first and second locations.

25. The method of claim 24, wherein the needle extends from a distal end of the guide device to extend through the chamber wall.

* * * * *

UNITED STATES PATENT AND TRADEMARK OFFICE
CERTIFICATE OF CORRECTION

PATENT NO. : 6,616,684 B1
DATED : September 9, 2003
INVENTOR(S) : Robert M. Vidlund et al.

It is certified that error appears in the above-identified patent and that said Letters Patent is hereby corrected as shown below:

<u>Title page,</u>
Item [75], Inventors, replace "Cyril J. Schweich, Jr., St. Paul, MN (US);" with
-- Cyril J. Schweich, Jr., Maple Grove, MN (US); --.

Item [*] Notice, replace "0 days." with -- 162 days. --

Signed and Sealed this

Thirteenth Day of April, 2004

JON W. DUDAS
*Acting Director of the United States Patent and Trademark Office*